United States Patent
Chen et al.

(10) Patent No.: US 11,957,767 B2
(45) Date of Patent: Apr. 16, 2024

(54) COMPOUND TARGETING PROSTATE SPECIFIC MEMBRANE ANTIGEN, AND PREPARATION METHOD AND APPLICATION THEREOF

(71) Applicant: YANTAI LANNACHENG BIOTECHNOLOGY CO., LTD., Shandong (CN)

(72) Inventors: Xiaoyuan Chen, Shandong (CN); Pengfei Xu, Shandong (CN)

(73) Assignee: YANTAI LANNACHENG BIOTECHNOLOGY CO., LTD., Shandong (CN)

( * ) Notice: Subject to any disclaimer, the term of this patent is extended or adjusted under 35 U.S.C. 154(b) by 0 days.

(21) Appl. No.: 18/548,546

(22) PCT Filed: Feb. 27, 2022

(86) PCT No.: PCT/CN2022/078129
§ 371 (c)(1),
(2) Date: Aug. 31, 2023

(87) PCT Pub. No.: WO2022/183993
PCT Pub. Date: Sep. 9, 2022

(65) Prior Publication Data
US 2024/0091389 A1 Mar. 21, 2024

(30) Foreign Application Priority Data
Mar. 1, 2021 (CN) .......................... 202110225558.X

(51) Int. Cl.
*A61K 51/04* (2006.01)
*A61P 35/00* (2006.01)
*C07D 257/02* (2006.01)

(52) U.S. Cl.
CPC .......... *A61K 51/0497* (2013.01); *A61P 35/00* (2018.01); *C07D 257/02* (2013.01)

(58) Field of Classification Search
CPC .... A61K 51/0497; A61P 35/00; C07D 257/02
See application file for complete search history.

(56) References Cited

FOREIGN PATENT DOCUMENTS

| | | |
|---|---|---|
| CN | 104650217 A | 5/2015 |
| CN | 109153641 A | 1/2019 |
| CN | 111741751 A | 10/2020 |
| CN | 113004371 A | 6/2021 |
| TW | 202005669 A | 2/2020 |
| WO | 2017/192874 A1 | 11/2017 |
| WO | 2019/165200 | 8/2019 |

OTHER PUBLICATIONS

International Search Report (with English translation) and Written Opinion issued in PCT/CN2022/078129, dated May 30, 2022, 14 pages.
Jie Zang et al., "177Lu-EB-PSMA Radioligand Therapy with Escalating Doses in Patients with Metastatic Castration-Resistant Prostate Cancer," Journal of Nuclear Medicine, Dec. 5, 2020, 61 (12): 1772-1778.
Zhantong Wang et al., "Single Low-Dose Injection of Evans Blue Modified PSMA-617 Radioligand Therapy Eliminates Prostate-Specific Membrane Antigen Positive Tumors," Bioconjugate Chem. 2018, 29, 3213-3221.
Notification to Grant issued in Chinese Application No. 202280003295.0, dated Aug. 8, 2023, with English translation (2 pages).
Office Action issued in Chinese Application No. 202280003295.0, dated Mar. 15, 2023, with English translation (12 pages).

*Primary Examiner* — Michael G. Hartley
*Assistant Examiner* — Leah H Schlientz
(74) *Attorney, Agent, or Firm* — HAMRE, SCHUMANN, MUELLER & LARSON, P.C.

(57) ABSTRACT

The present disclosure provides a compound targeting prostate specific membrane antigen (PSMA), wherein the compound has the following structure shown in Formula (I); $R_1$ is a compound structure targeting prostate specific membrane antigen; $L_1$ is $-(X)_n-(CH_2)_m-(Y)_q-$, X and Y are independently selected from lysine, glutamic acid or a derivative structure containing lysine and glutamic acid, n is an integer from 0 to 12, m is an integer from 0 to 60, q is an integer from 0 to 12, and each $CH_2$ may be individually substituted with $-O-$, $-NH(CO)-$, or $-(CO)-NH-$; $L_2$ is $-(CH_2)_p-$, p is an integer from 0 to 30, and each $CH_2$ may be individually substituted with $-O-$, $-NH(CO)-$, or $-(CO)-NH-$; and $R_2$ is a nuclide chelating group. The present disclosure also provides a radiolabeled complex based on the structure of the compound. The compound and the radiolabeled complex have appropriate blood circulation time, high uptake in tumors and long retention time, and are suitable for nuclide therapy and imaging of tumors with high expression of PSMA.

Formula (I)

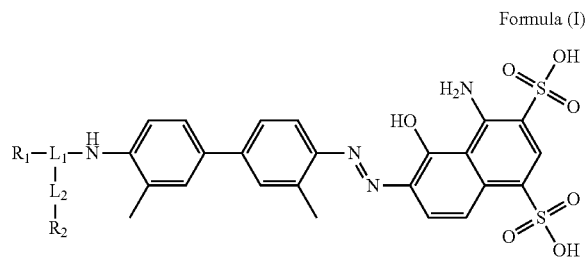

8 Claims, 8 Drawing Sheets

COMPOUND TARGETING PROSTATE SPECIFIC MEMBRANE ANTIGEN, AND PREPARATION METHOD AND APPLICATION THEREOF

TECHNICAL FIELD

The present disclosure relates to the fields of nuclear medicine and molecular imaging, and specifically relates to a compound targeting prostate specific membrane antigen, preparation and radiolabeling and application thereof.

BACKGROUND

Prostate cancer is the second most common cancer among men in the global world and the sixth most common cancer among men in China. In the last ten years, the incidence of the prostate cancer in China has been increasing rapidly, and the average annual increase rate has already reached 12.07%. The prostate cancer is described as a "silent killer" that is not easily detected in the early stage, and about two thirds of patients have reached the terminal stage during diagnosis. The expression of a prostate specific membrane antigen (PSMA) in prostate cancer cells is 100 to 1,000 times higher than that in normal cells and is even higher in cancer cells in terminal cancer and anti-androgen therapy. Due to these characteristics, the PSMA becomes an ideal target for targeted diagnosis and therapy of the prostate cancer.

In December 2020, 68-gallium labeled PSMA-11 ($^{68}$Ga-PSMA-11) was approved by the Food and Drug Administration of the United States, which is the first PET imaging diagnostic agent for PSMA positive lesions of patients suffered from the prostate cancer. Subsequently, 177-Lu labeled PSMA617 was applied to therapeutic research of the PSMA positive lesions. As a small-molecule medicine, $^{177}$Lu-PSMA617 is rapidly eluted in the blood. Due to such metabolic characteristics, the dose uptake is low at a tumor site, and the retention time is too short. About 30% of patients have no response to therapy with the $^{177}$Lu-PSMA617. To increase the dose delivered to tumors, studies have been carried out to connect maleimide modified truncated Evans Blue with sulfhydryl-containing PSMA ($^{177}$Lu-EB-PSMA617). Through binding to albumin in the blood, the half-life of a PSMA-targeted probe in circulation is significantly prolonged. Although the modification strategy has increased the dose uptake in tumors and prolonged the retention time in tumors, new problems are found in subsequent studies. Among patients accepting the therapy with $^{177}$Lu-EB-PSMA617 (3.52±0.58 GBq), 37.5% of the patients have 3- to 4-level anemia, 12.5% of the patients have decreased white blood cells, and 37.5% of the patients have thrombocytopenia (Journal of Nuclear Medicine December 2020, 61 (12): 1772-1778). This situation indicates that the too long half-life of the $^{177}$Lu -EB-PSMA617 in the blood leads to hematotoxicity and myelosuppression, and especially has more serious side effects to patients suffered from the prostate cancer with a heavy burden of bone metastasis and critical bone marrow functions. Due to such serious side effects, the value of a targeted medicine in clinical application will be greatly reduced. Through these studies, people have realized that a targeted probe having a longer half-life in blood circulation for therapy of tumors is not better, and on the contrary, the blood circulation time is controlled within a reasonable range while high uptake in tumors is ensured.

Therefore, a PSMA-targeted probe needs to be further optimized, and the blood circulation time is adjusted within an appropriate range while high uptake in tumors is satisfied, as to meet the needs of nuclide therapy and achieve maximum therapeutic benefits.

SUMMARY

Based on the above background, a primary purpose of the present disclosure is to develop a compound targeting prostate specific membrane antigen. The compound has high uptake in tumors and appropriate blood circulation time. Not only can the defects of too fast metabolism and too short retention time at a target organ of existing small-molecule $^{177}$Lu-PSMA617 be overcome, but also hematotoxicity and myelosuppression caused by a too long half-life of molecule like $^{177}$Lu-EB-PSMA617 in the blood can be avoided. Thus, nuclide diagnosis and therapy effects of targeting PSMA are improved, and the compound has real value and potential in clinical application and popularization.

Another purpose of the present disclosure is to provide a radiolabeled complex targeting prostate specific membrane antigen. The complex also has high uptake in tumors and appropriate blood circulation time and can have the advantages of a high tumor therapeutic effect and low side effects.

Another purpose of the present disclosure is to provide a preparation method of the radiolabeled complex targeting prostate specific membrane antigen.

Another purpose of the present disclosure is to provide application of the complex in nuclide imaging and therapy of targeting prostate cancer.

Technical solutions for realizing the above primary purpose of the present disclosure include the following two aspects: synthesis of the following ligands and radiolabeling thereof.

In the first aspect, the present disclosure provides a compound targeting prostate specific membrane antigen having high uptake in tumors and appropriate blood circulation time. The compound has the following structure shown in Formula (I):

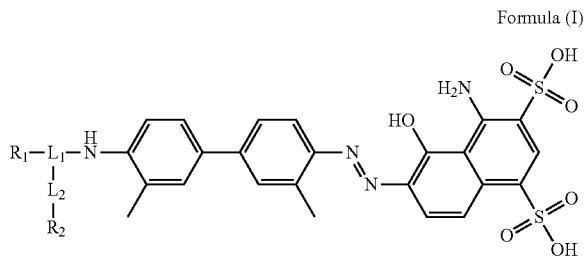

Formula (I)

wherein $L_1$ is -(X)$_n$-(CH$_2$)$_m$-(Y)$_q$-, wherein n is an integer from 0 to 12 (preferably an integer from 0 to 6), X and Y are independently selected from lysine, glutamic acid or a derivative structure containing lysine and glutamic acid, m is an integer from 0 to 60 (preferably an integer from 0 to 30), q is an integer from 0 to 12 (preferably an integer from 0 to 6), wherein each CH$_2$ may be individually substituted with —O—, —NH(CO)—, or —(CO)—NH—;

$L_2$ is -(CH$_2$)$_p$-, wherein p is an integer from 0 to 30 (preferably an integer from 0 to 12), wherein each CH$_2$ may be individually substituted with —O—, —NH(CO)—, or —(CO)—NH—, provided that no two adjacent CH$_2$ groups are substituted;

$R_1$ is derived from a compound targeting prostate specific membrane antigen, and has any one of the following structures:
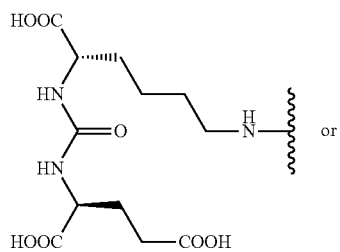
or
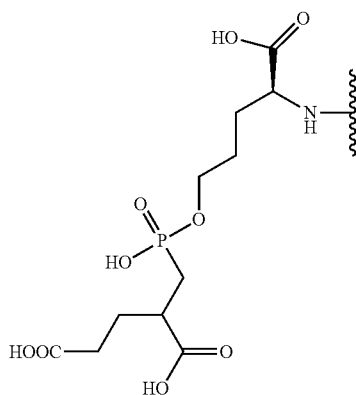
;
and $R_2$ is a nuclide chelating group, and is selected from any one of the following structures:
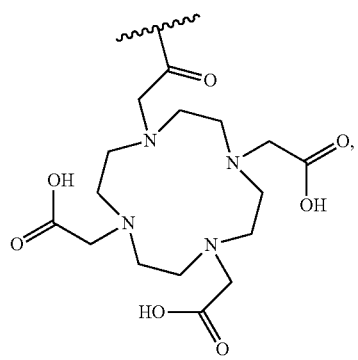
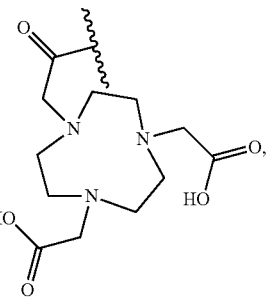
,
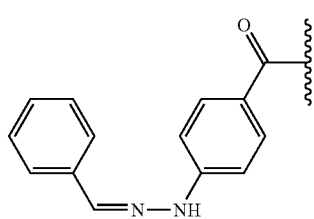
,
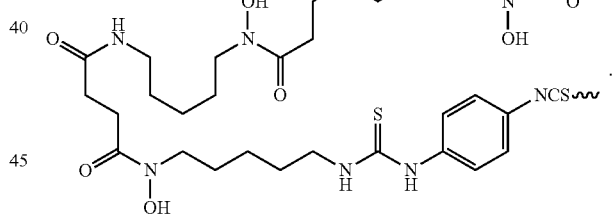
, or
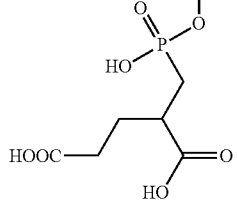
.
In a solution of the present disclosure, the $R_1$ in Formula (I) is preferably selected from:
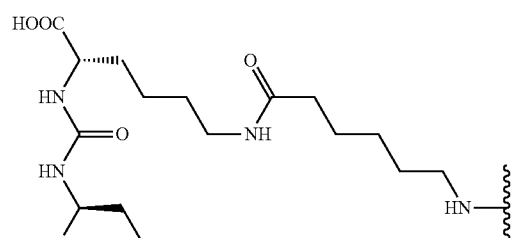
,
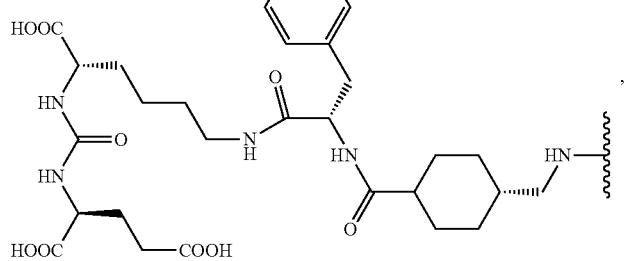
, -continued
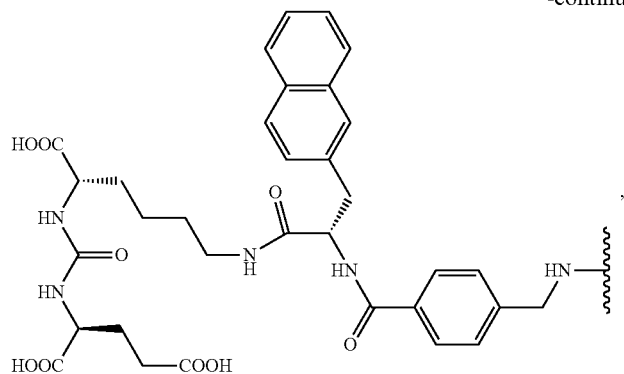
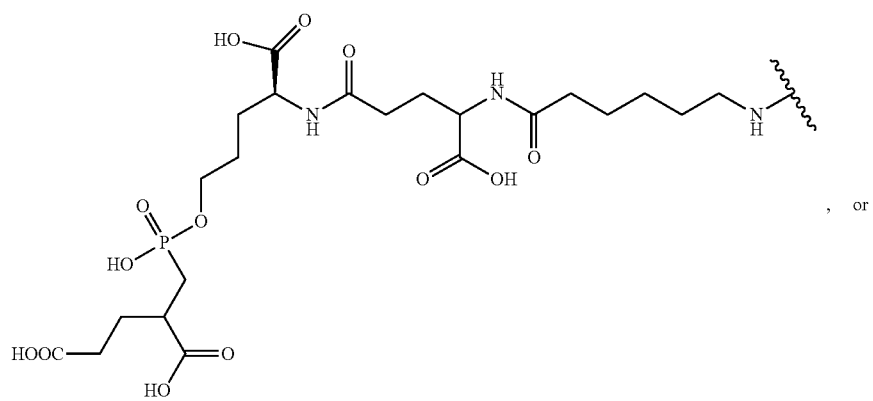
, or
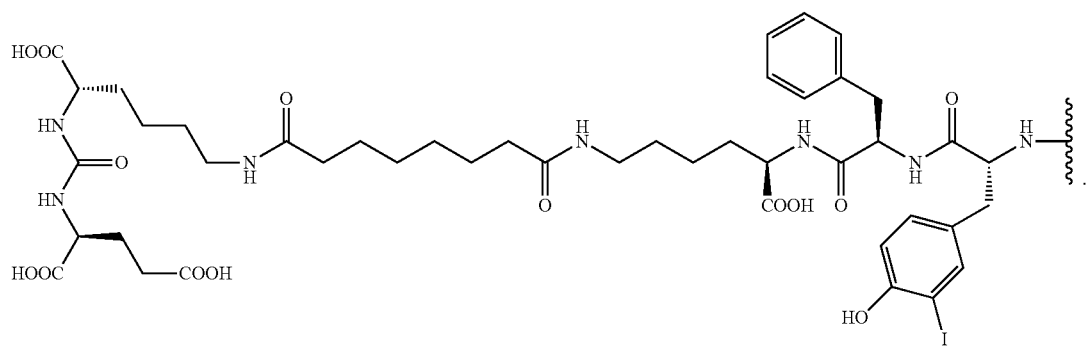
.
In a preferred solution of the present disclosure, the $R_1$ in Formula (I) is
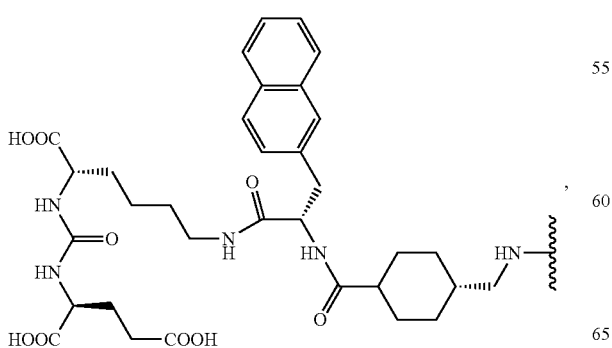
,
and the $R_2$ is That is to say, the compound has the
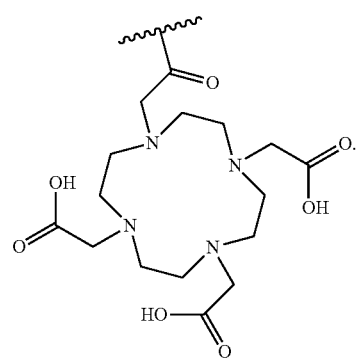 [SMILES: *C(=O)CN1CCN(CC(=O)O)CCN(CC(=O)O)CCN(CC(=O)O)CC1]

following structure shown in Formula (II):

Formula (II)

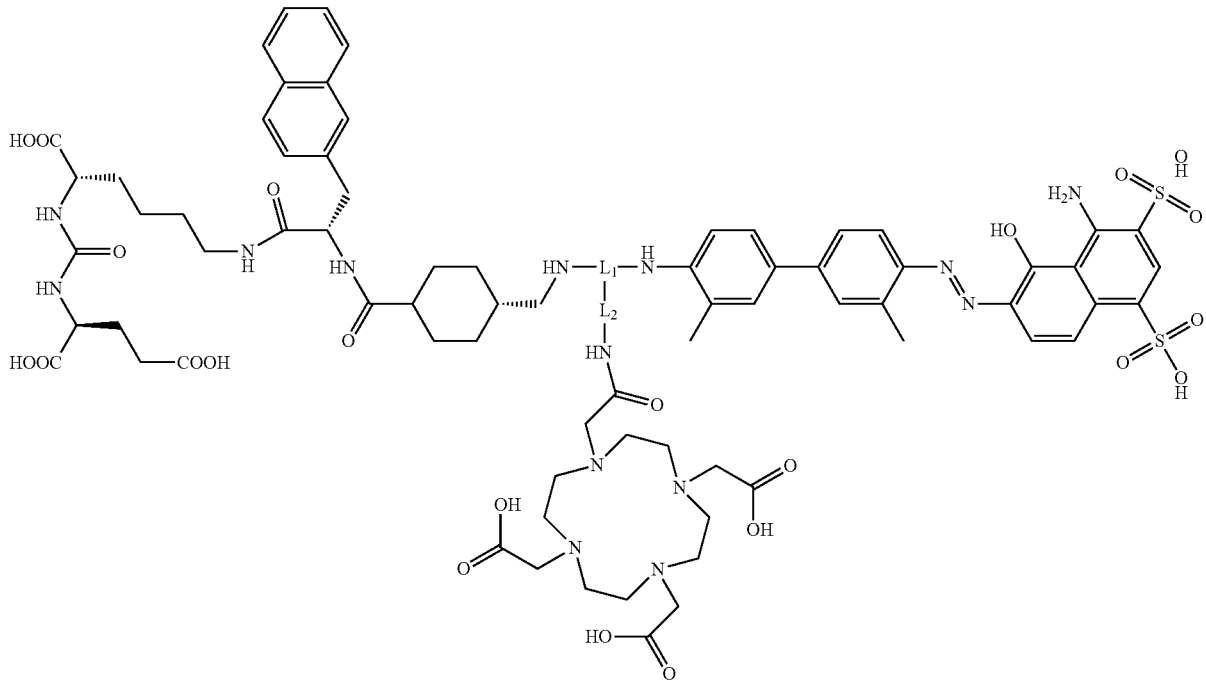

wherein L$_1$ is preferably selected from:
-Lys—(CO)—CH$_2$CH$_2$—(CO)—NH—CH$_2$—(CO)—,
-Lys—(CO)—CH$_2$CH$_2$—(OCH$_2$CH$_2$)—(CO)—NH—CH$_2$—(CO)—,
-Lys—(CO)—CH$_2$CH$_2$—(OCH$_2$CH$_2$)$_2$—(CO)—NH—CH$_2$—(CO)—,
-Lys—(CO)—CH$_2$CH$_2$—(OCH$_2$CH$_2$)$_4$—(CO)—NH—CH$_2$—(CO)—,
—(CO)—CH$_2$CH$_2$—(CO)-Lys-,
—(CO)—CH$_2$CH$_2$—(OCH$_2$CH$_2$)—(CO)-Lys-,
—(CO)—CH$_2$CH$_2$—(OCH$_2$CH$_2$)$_2$—(CO)-Lys-,
—(CO)—CH$_2$CH$_2$—(OCH$_2$CH$_2$)$_4$-Lys-,
-Lys—(CO)—CH$_2$—(CO)—NH—CH$_2$—(CO)—,
-Lys—(CO)—CH$_2$—(OCH$_2$CH$_2$)—O—CH$_2$(CO)—NH—CH$_2$—(CO)—,
-Lys—(CO)—CH$_2$—(OCH$_2$CH$_2$)$_3$—O—CH$_2$(CO)—NH—CH$_2$—(CO)—,
—(CO)—CH$_2$—(CO)-Lys-,
—(CO)—CH$_2$—(OCH$_2$CH$_2$)—O—CH$_2$(CO)-Lys-, or
—(CO)—CH$_2$—(OCH$_2$CH$_2$)$_3$—O—CH$_2$(CO)-Lys-.

In a further preferred solution of the present disclosure, the compound has the following structure shown in Formula (II-1):

Formula (II-1)

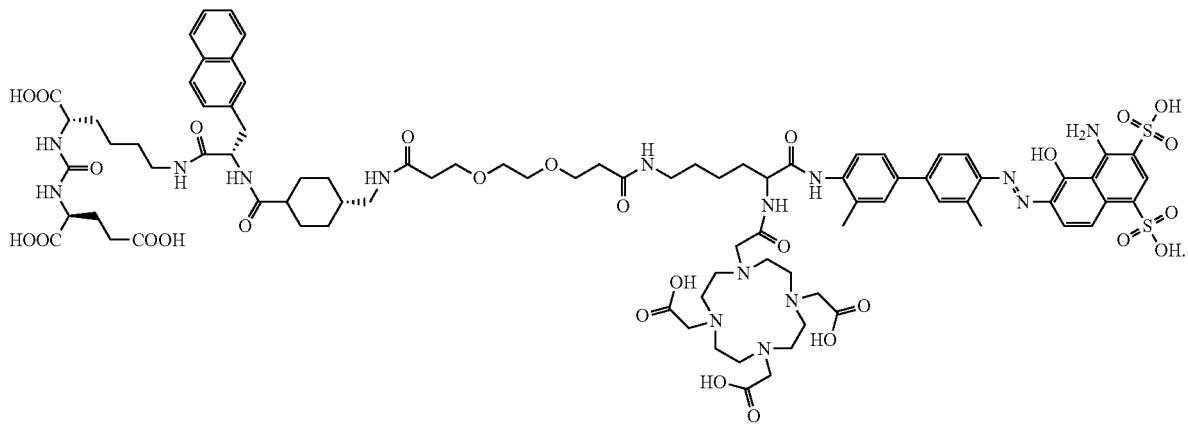

In a preferred solution of the present disclosure, the compound may also have any one of the following structures shown in Formula (II-2) to Formula (II-8):

Formula (II-2)
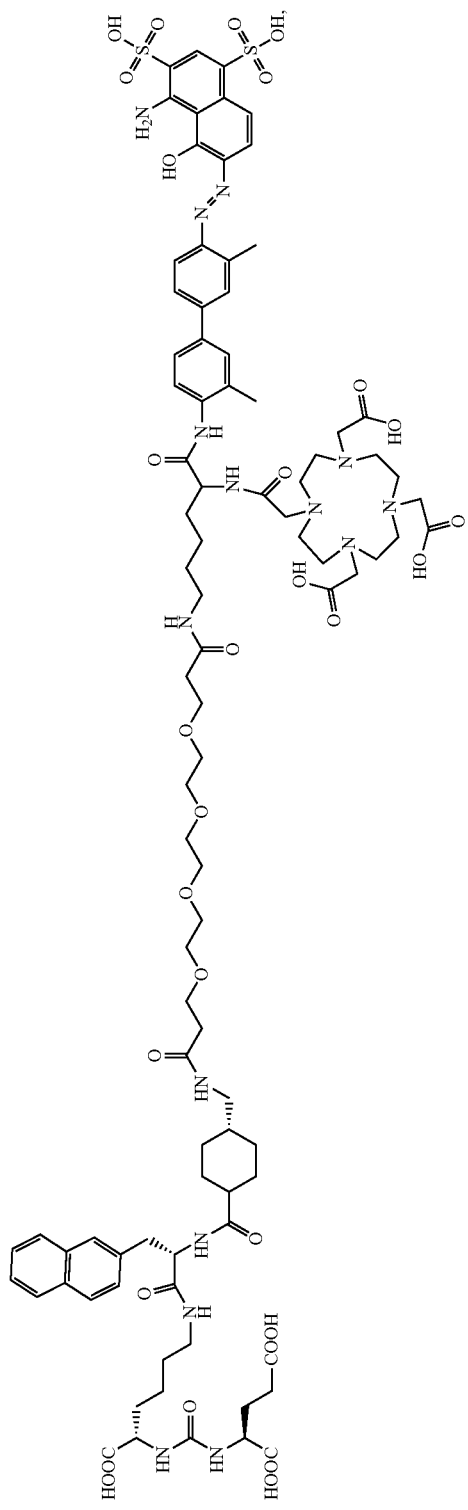

-continued
Formula (II-3)
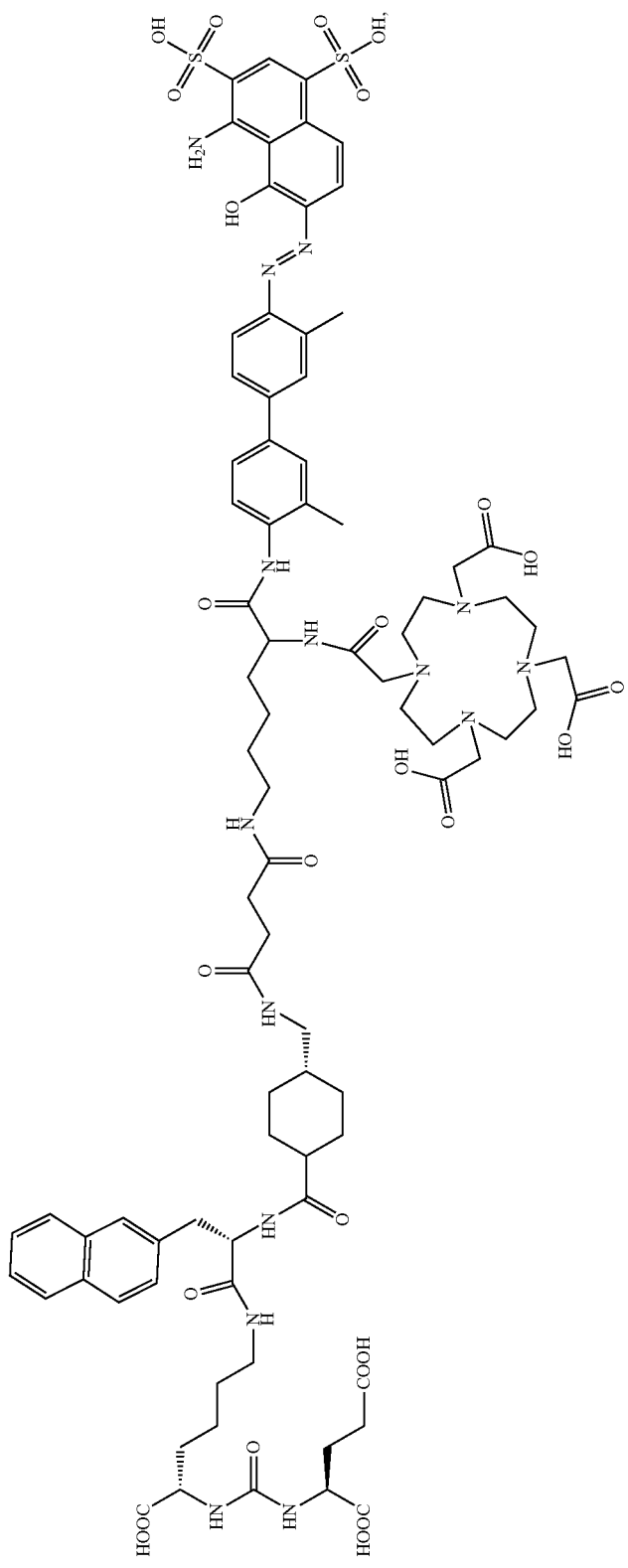
Formula (II-4)
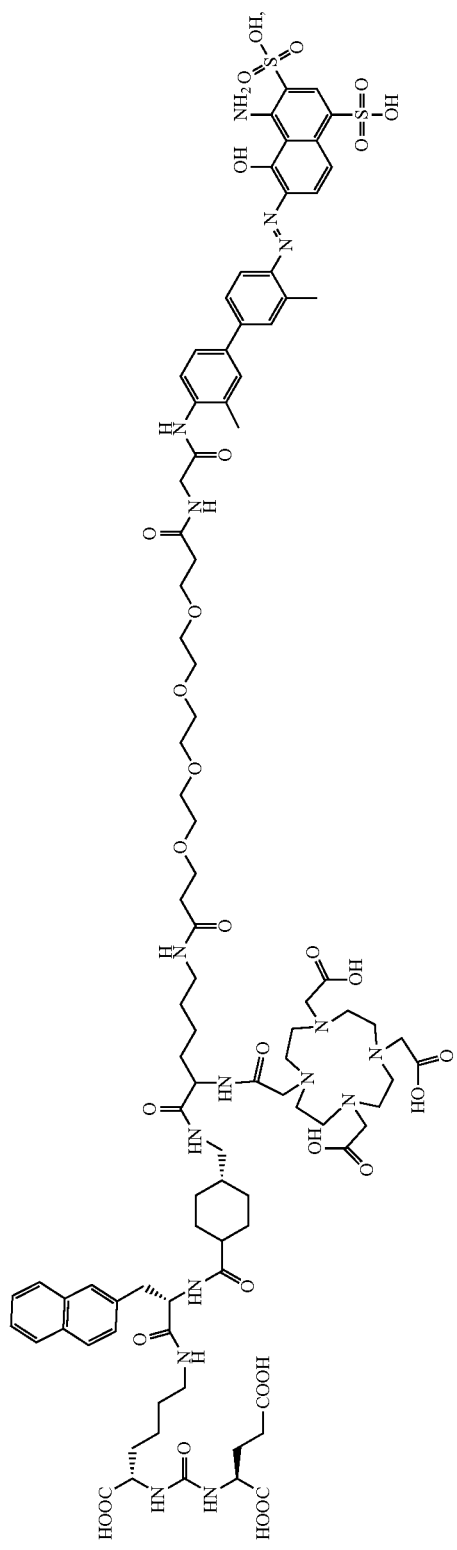

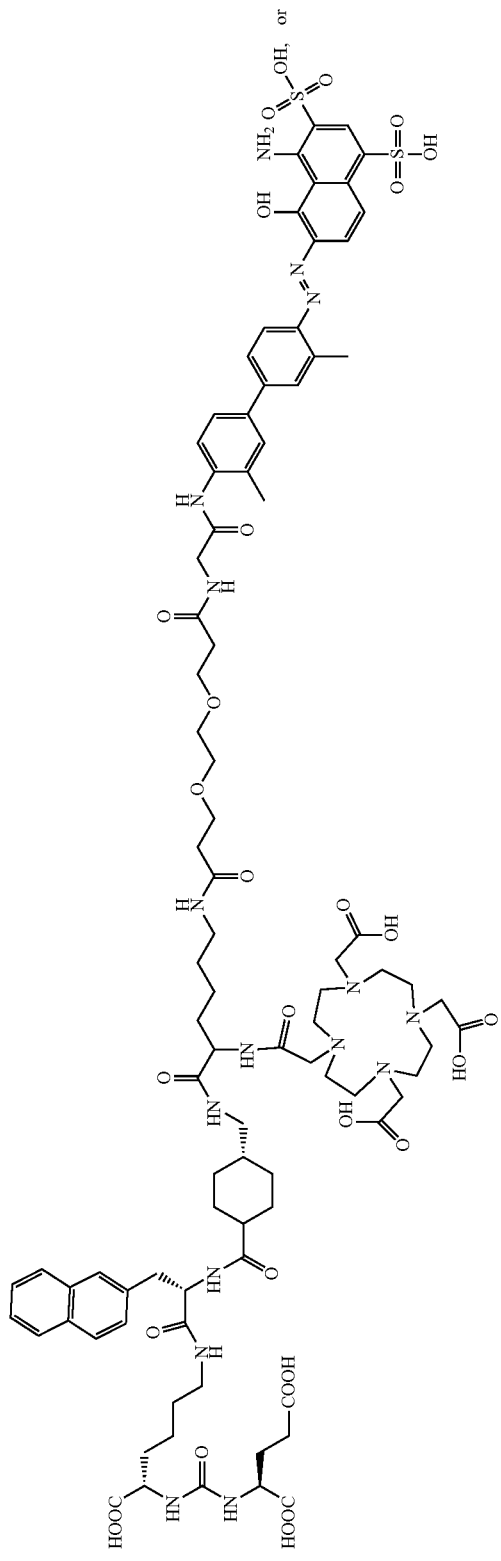
Formula (II-5)
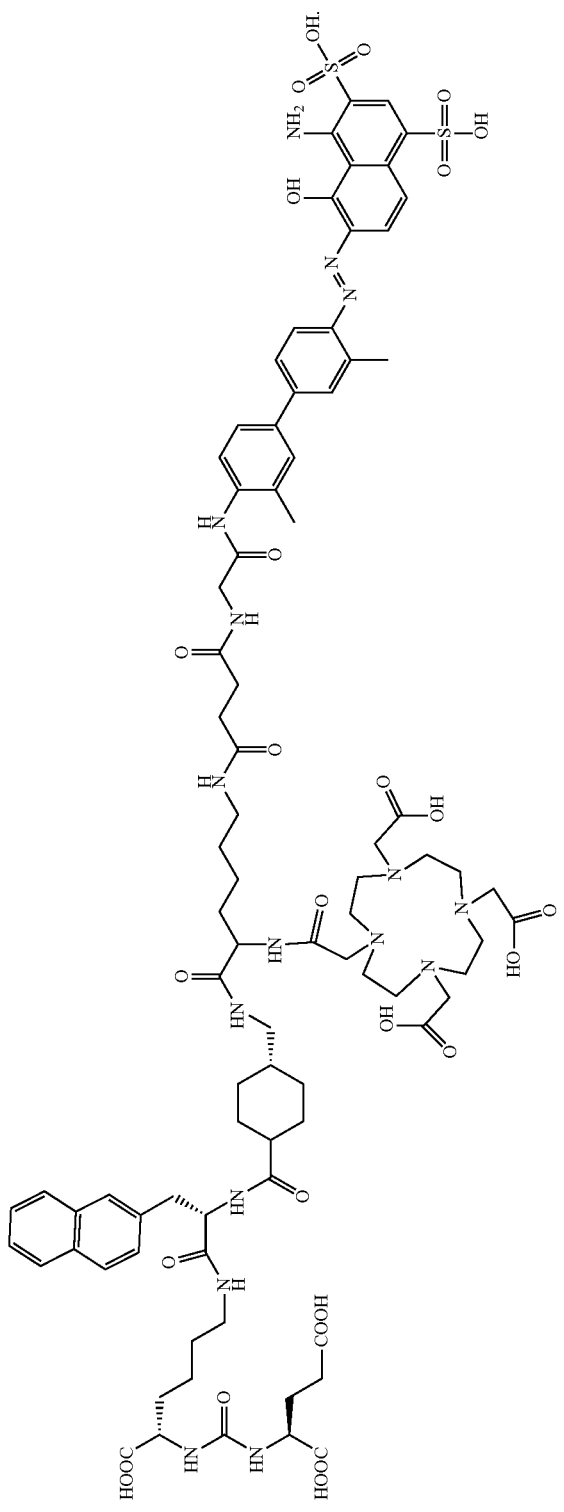
Formula (II-6)

On the above basis, the present disclosure further provides a method for preparing the compound shown in Formula (II-1). The method includes the following steps:

introducing a Boc protective group to one end of 4,4'-diamino-3,3'-dimethyl biphenyl, followed by a reaction with 4,6-diamino-5-hydroxy-1,3-naphthalenedisulfonic acid to prepare a truncated Evans Blue derivative; removing the Boc protective group, followed by an amide condensation reaction with Nα-Fmoc-Nε-Boc-L-lysine; next, removing the Boc protective group under the action of TFA, followed by a reaction with COOH-PEG$_2$-COOH and a reaction with PSMA-617 under the presence of EDC and NHS; then removing an Fmoc protective group using piperazine; and finally, carrying out a reaction with DOTA-NHS to obtain a compound having the following structure shown in Formula (II-1).

A preferred method for preparing the compound shown in Formula (II-1) of the present disclosure specifically includes the following steps:

Reacting 4,4'-diamino-3,3'-dimethyl biphenyl (compound 1) with di-tert-butyl dicarbonate to obtain a compound 2; reacting the compound 2 with 4,6-diamino-5-hydroxy-1,3-naphthalenedisulfonic acid and sodium nitrite to prepare a truncated Evans Blue derivative (compound 3); removing a Boc protective group of the compound 3 to obtain a compound 4; reacting the compound 4 with Nα-Fmoc-Nε-Boc-L-lysine under presence of HATU and DIPEA by condensation to obtain a compound 5; dissolving the compound 5 in a trifluoroacetic acid solution for removing a protective group to obtain a compound 6; dissolving the compound 6 in N,N-dimethylformamide, and carrying out a reaction with COOH-PEG$_2$-COOH under the presence of HATU to obtain a compound 7; next, carrying out a reaction with PSMA-617 under the presence of EDC and NHS to obtain a compound 8; then removing an Fmoc protective group using piperazine to obtain a compound 9; and finally, carrying out a reaction with DOTA-NHS to obtain a compound 10 having the following structure shown in Formula (II-1).

A synthesis route in the above specific steps is as follows:

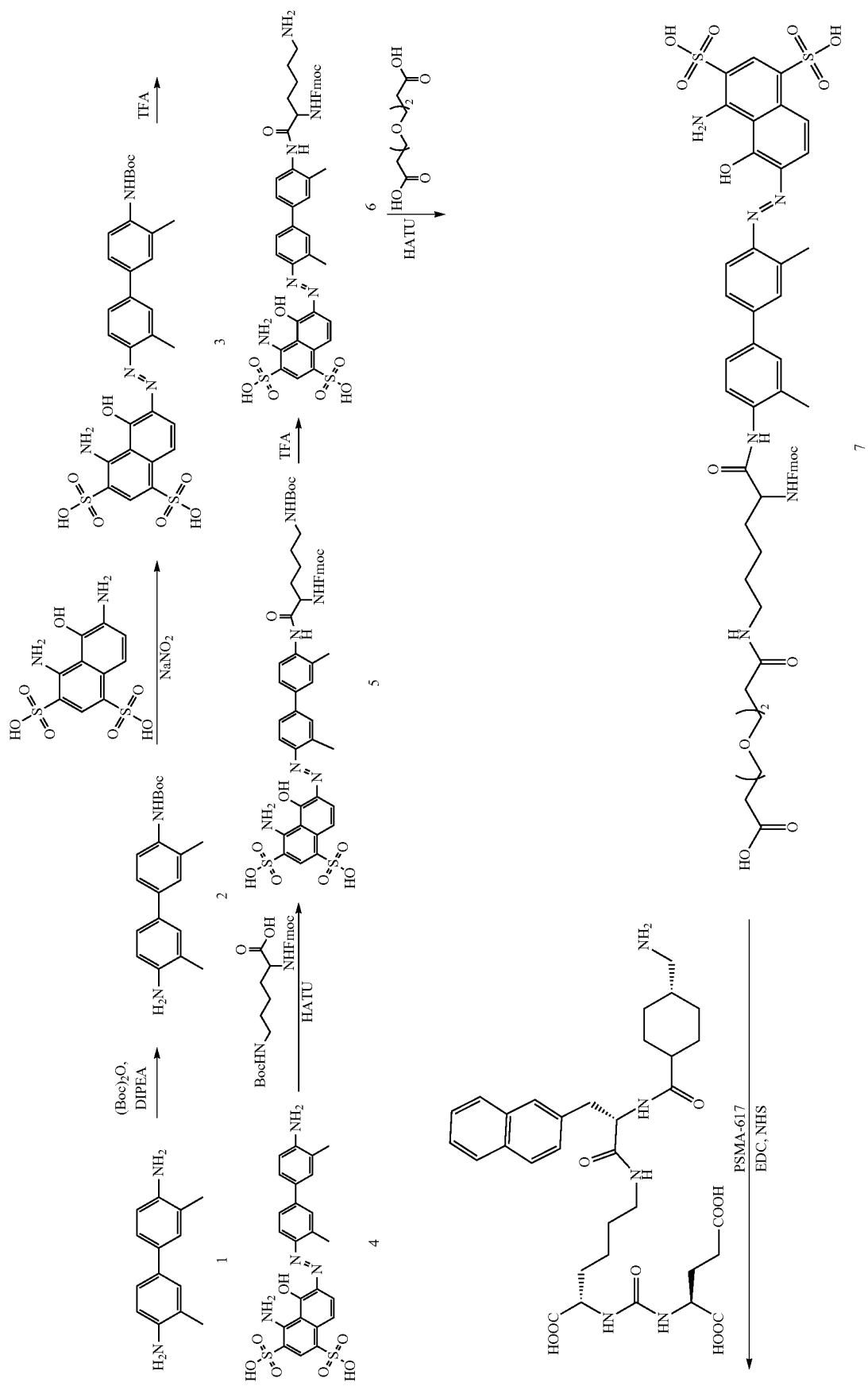

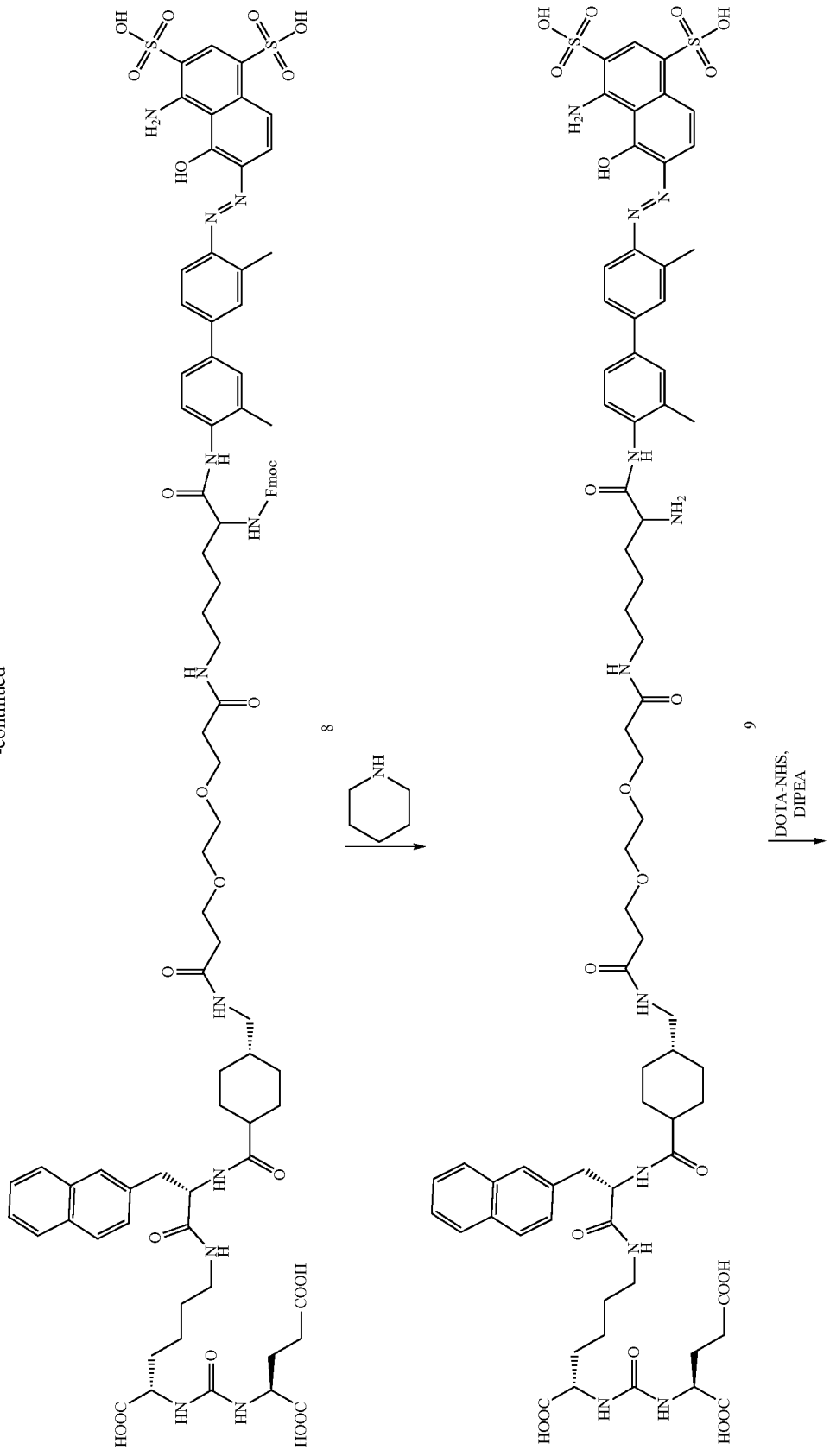

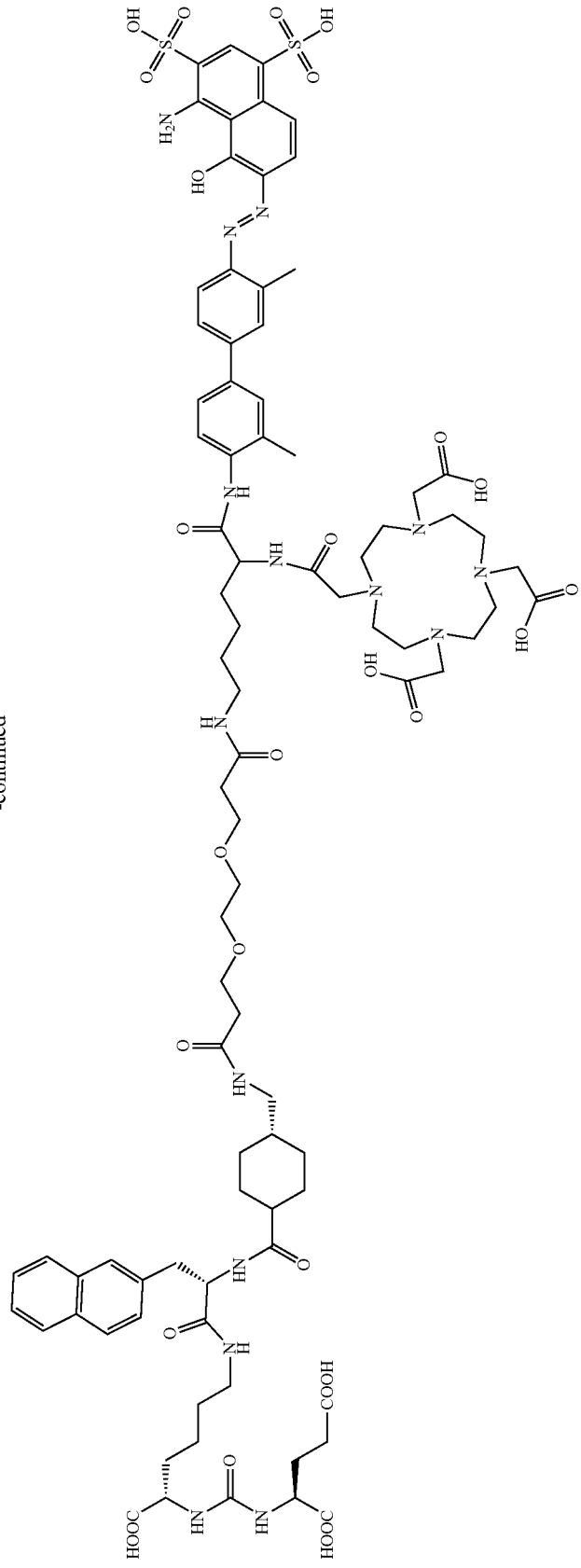

Preparation methods of other compounds in solutions of the present disclosure are similar to the preparation method of the compound 10, and preparation can be carried out basically based on an existing conventional means with reference to the synthesis route of the compound 10.

In another aspect, the present disclosure further provides a radiolabeled complex. The complex is obtained by using the compound shown in Formula (I) of the present disclosure as a ligand and labeling the ligand with a radionuclide. The radiolabeled complex can be used as a novel radioactive diagnostic and therapeutic probe for tumors, namely, a radionuclide diagnostic probe or a radionuclide therapeutic probe. The nuclide may be selected from any one of $^{177}$Lu, $^{90}$Y, $^{18}$F, $^{64}$Cu, $^{68}$Ga, $^{62}$Cu, $^{67}$Cu, $^{86}$Y, $^{89}$Zr, $^{99m}$Tc, $^{89}$Sr, $^{153}$Sm, $^{149}$Tb, $^{161}$Tb, $^{186}$Re, $^{188}$Re, $^{212}$Pb, $^{213}$Bi, $^{223}$Ra, $^{225}$Ac, $^{226}$Th, $^{227}$Th, $^{131}$I, $^{121}$At, or $^{111}$In, and is preferably $^{68}$Ga, $^{177}$Lu, or $^{90}$Y.

The complex of the present disclosure preferably has the following structure shown in Formula (III):

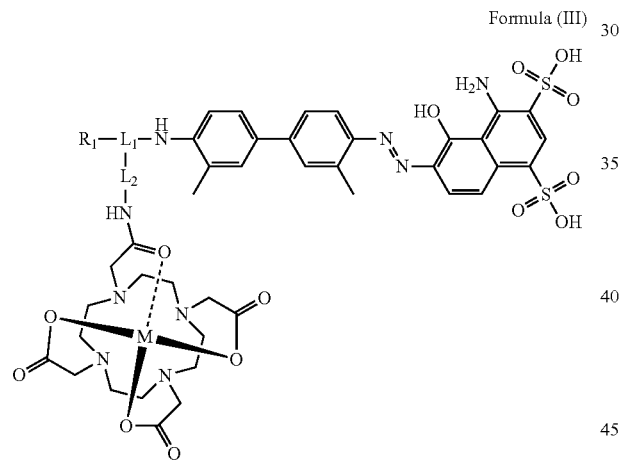

Formula (III)

wherein
$L_1$ is $-(X)_n-(CH_2)_m-(Y)_q-$, wherein n is an integer from 0 to 12 (preferably an integer from 0 to 6), X and Y are independently selected from lysine, glutamic acid or a derivative structure containing lysine and glutamic acid, m is an integer from 0 to 60 (preferably an integer from 0 to 30), q is an integer from 0 to 12 (preferably an integer from 0 to 6), wherein each $CH_2$ may be individually substituted with —O—, —NH(CO)—, or —(CO)—NH—; $L_2$ is $-(CH_2)_p-$, wherein p is an integer from 0 to 30 (preferably an integer from 0 to 12), wherein each $CH_2$ may be individually substituted with —O—, —NH(CO)—, or —(CO)—NH—, provided that no two adjacent $CH_2$ groups are substituted;

$R_1$ is a compound structure targeting prostate specific membrane antigen, which contains a structure of

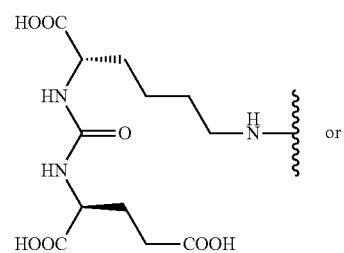 or

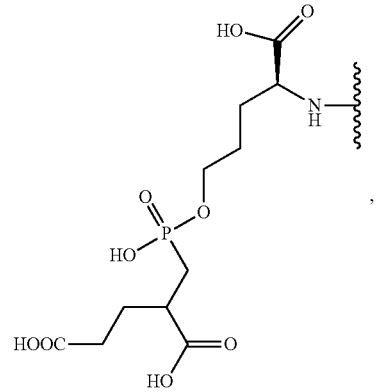, and is preferably selected from:

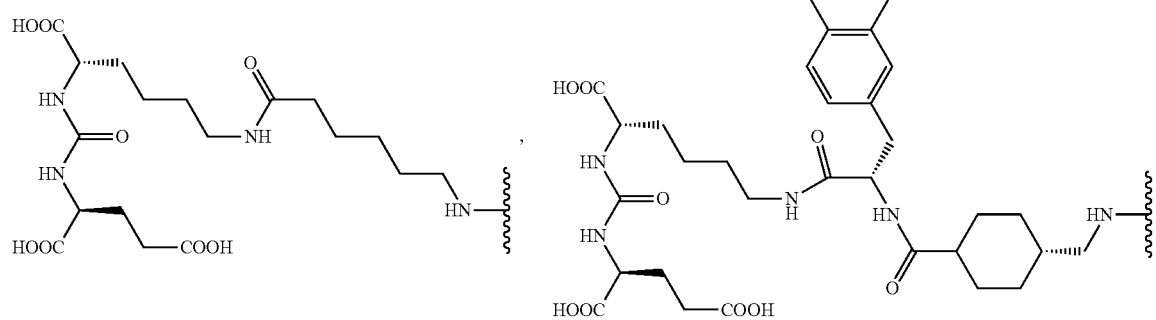

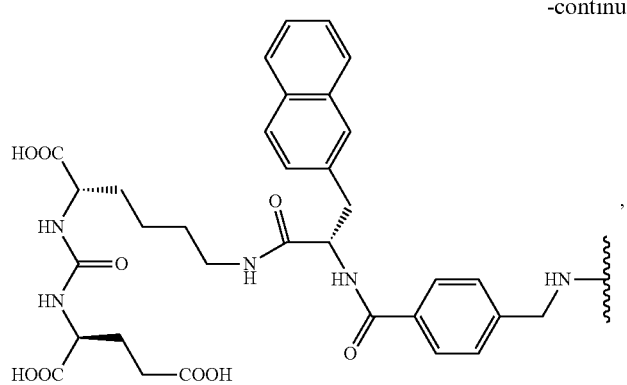

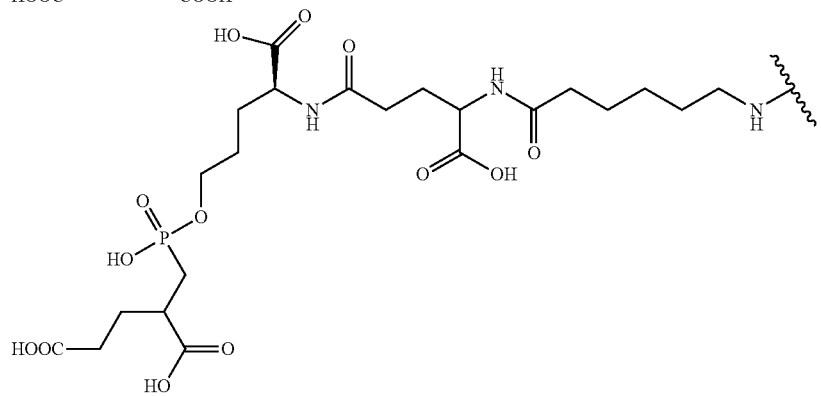

, or

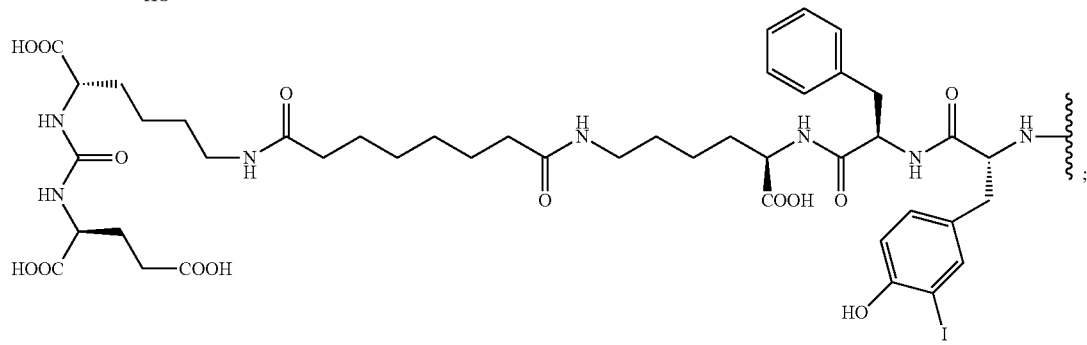

;

and M is a radionuclide selected from any one of $^{68}$Ga, $^{177}$Lu, or $^{90}$Y.

The radiolabeled complex of the present disclosure can be prepared from a compound containing a radionuclide and the compound shown in Formula (I) of the present disclosure by a variety of existing labeling methods. A labeling method of the present disclosure preferably includes the following wet method or freeze-drying method.

A wet labeling solution includes: dissolving an appropriate amount of the compound shown in Formula (I) of the present disclosure in a buffer solution or deionized water; and adding a radionuclide solution to a resulting solution for a reaction under closed conditions for 5-40 min to produce a radionuclide labeled complex;

or a freeze-drying labeling solution includes: dissolving an appropriate amount of the compound shown in Formula (I) of the present disclosure in a buffer solution or deionized water; treating the obtained solution to aseptic filtration, followed by loading into a container, freeze-drying and sealing with a stopper to obtain a freeze-dried medicine box; and then adding an appropriate amount of an acetic acid solution or a buffer solution to the freeze-dried medicine box for dissolution, and adding a corresponding radionuclide solution for a reaction under closed conditions for 5-40 min to produce a radionuclide labeled complex. The container for loading is preferably a frozen storage tube or a controlled antibiotic bottle. An excipient, such as mannitol and ascorbic acid, can also be added to the medicine box according to the forming situation of a freeze-dried powder in the medicine box, and the medicine box can achieve an optimal forming effect by adjusting the dose of the compound shown in Formula (I) of the present disclosure and the excipient.

Products obtained according to the wet labeling solution and the freeze-drying labeling solution can be further prepared into injections by conventional treatment (such as chromatographic separation and purification, rotary evaporation to remove the solvent, dissolution of residues with PBS or water or normal saline, and aseptic filtration).

In a preferred specific embodiment of the present disclosure, with the compound 10 shown in Formula (II-1) as a ligand, a preferred preparation method of a radiolabeled compound 10 is a wet labeling method. The method includes the following steps: dissolving the compound 10 in a buffer solution or deionized water; adding a fresh radioactive solution for a reaction under closed conditions at 37-90° C. for 5-40 min, followed by cooling; adding water for diluting a reaction solution, followed by separation and purification with a Sep-Pak C18 chromatographic column; rinsing the chromatographic column with a buffer solution or water to remove unreacted radioactive ions; and conducting rinsing with a hydrochloric acid-ethanol solution or an ethanol solution, and conducting dilution with normal saline or PBS, followed by aseptic filtration to obtain an injection of a radiolabeled complex having the structure shown in Formula (IV), where a radionuclide M is $^{68}$Ga, $^{177}$Lu, or $^{90}$Y.

Another preferred preparation method of a radiolabeled compound 10 of the present disclosure is a freeze-drying labeling method. The method includes: dissolving the compound 10 and other necessary reagents in a buffer solution, and treating the obtained solution to aseptic filtration, followed by loading into a frozen storage tube, freeze-drying and sealing to obtain a freeze-dried medicine box; adding an appropriate amount of a buffer solution to the freeze-dried medicine box for dissolution, and adding a newly prepared radioactive solution for a reaction under closed conditions at 37-120° C. for 5-40 min, followed by cooling; adding water for diluting a reaction solution, followed by separation and purification with a Sep-Pak C18 chromatographic column; rinsing the chromatographic column with a buffer solution or water to remove unreacted radioactive ions; and conducting rinsing with a hydrochloric acid-ethanol solution or an ethanol solution, and conducting dilution with normal saline or PBS, followed by aseptic filtration to obtain an injection of a radiolabeled complex having the structure shown in Formula (IV), where a radionuclide M is $^{68}$Ga, $^{177}$Lu, or $^{90}$Y.

Other chemicals used in the above synthesis steps are commercially available products.

The buffer solution is a substance for stabilizing the pH value of a reaction solution, and may be acetate, lactate, tartrate, malate, maleate, succinate, ascorbate, carbonate, phosphate and a mixture thereof.

In another aspect, the present disclosure also provides application of the compound shown in Formula (I) or a pharmacologically acceptable salt thereof in preparation of medicines in nuclide therapy or imaging of tumors with high expression of PSMA in mammals.

The present disclosure also provides application of the radiolabeled complex shown in Formula (III) in nuclide therapy and imaging of tumors with high expression of PSMA in mammals.

In preferred application of the present disclosure, the complex is formulated as an injection, and then intravenously injected into human patients or mammals with tumors with high expression of PSMA.

The present disclosure provides a compound targeting prostate specific membrane antigen having high uptake in tumors and appropriate blood circulation time and a radionuclide labeled complex thereof, and also provides a preparation method and a labeling method of the compound. Biological test results show that the compound has an appropriate half-life in blood circulation, high uptake in tumors and long retention time. Such excellent properties are not available in other PSMA targeting agents at present, and the compound is suitable for nuclide therapy and imaging of tumors with high expression of PSMA.

Formula (IV)

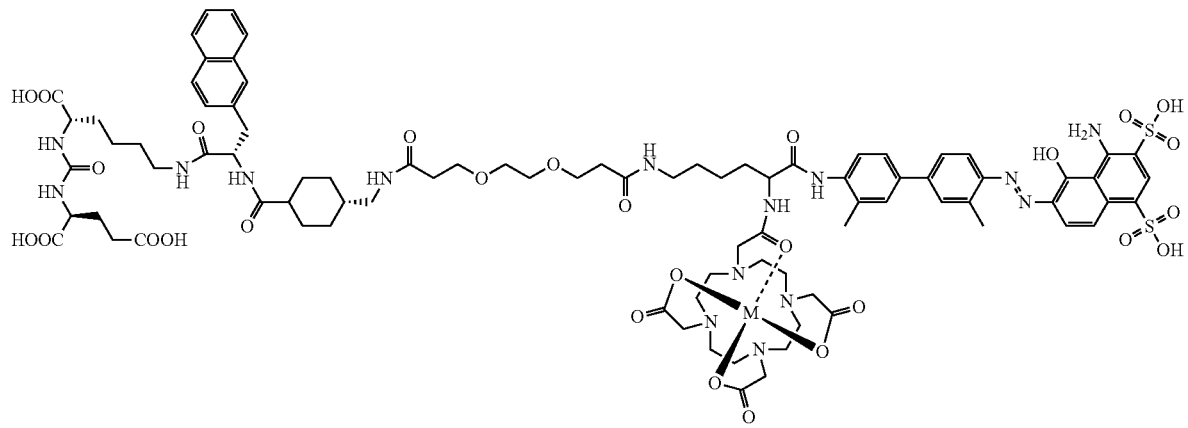

Figure 5:
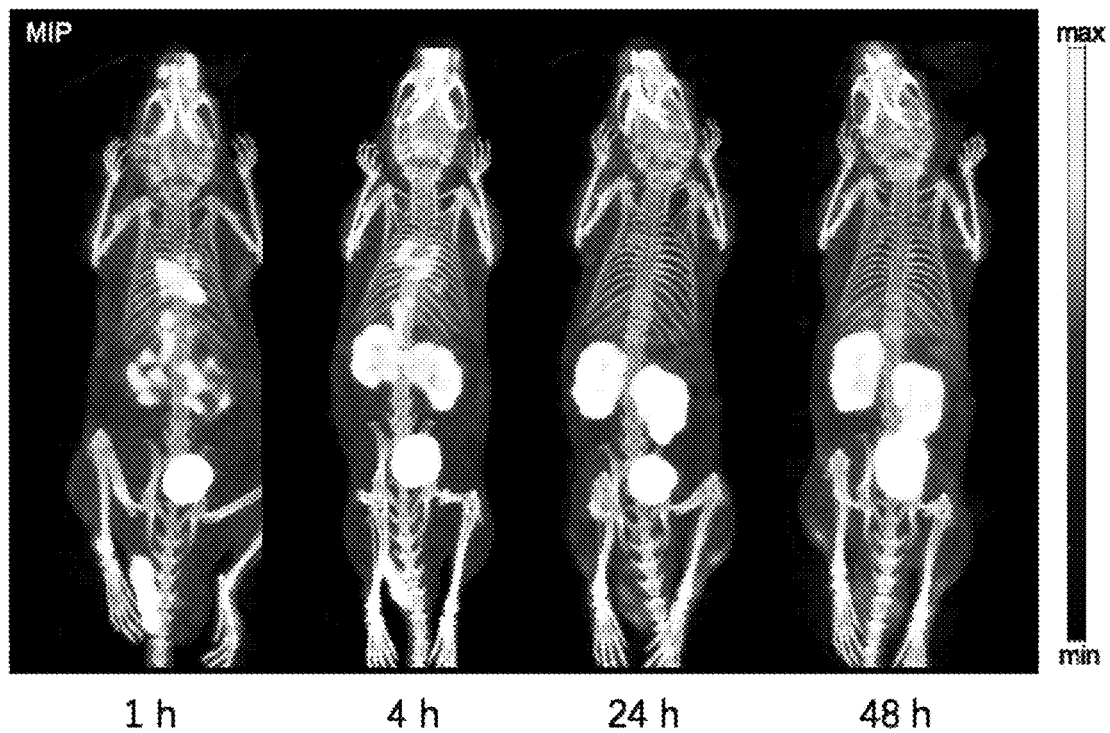

FIG. 5 is a diagram showing SPECT-CT imaging of normal mice at different time points after the compound in Example 31 is injected.

Figure 6:
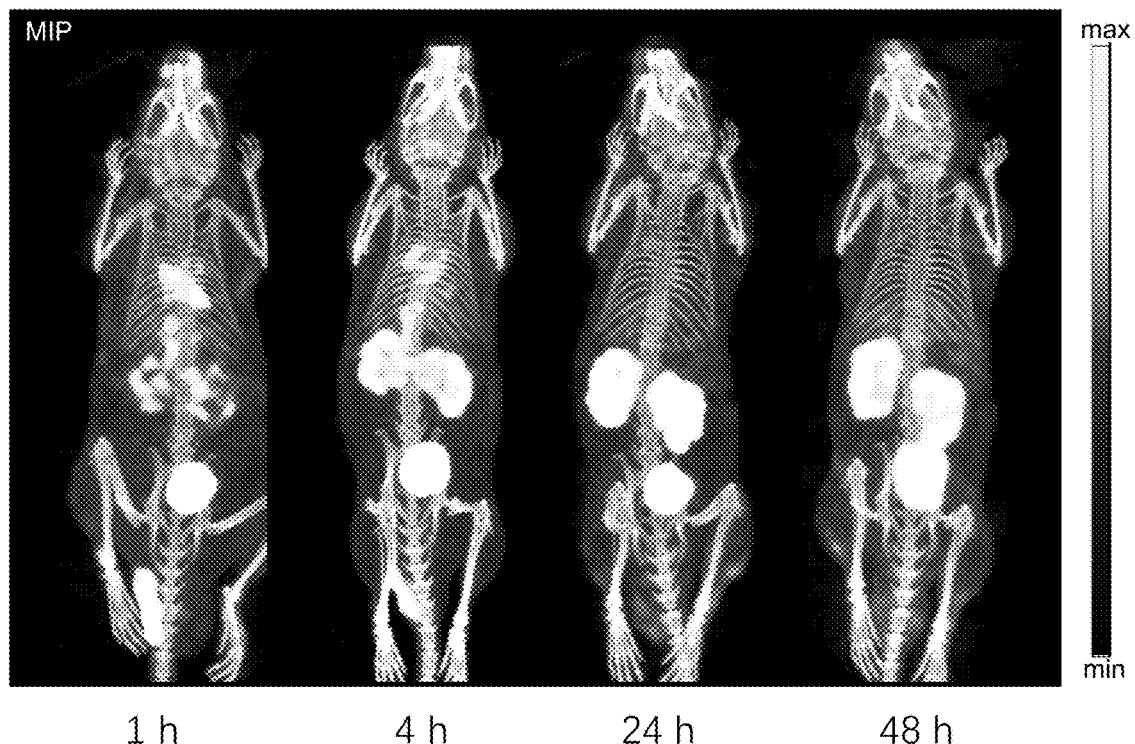

FIG. 6 is a diagram showing SPECT-CT imaging of normal mice at different time points after $^{177}$Lu labeled compound (II-2) in an example is injected.

Figure 7:
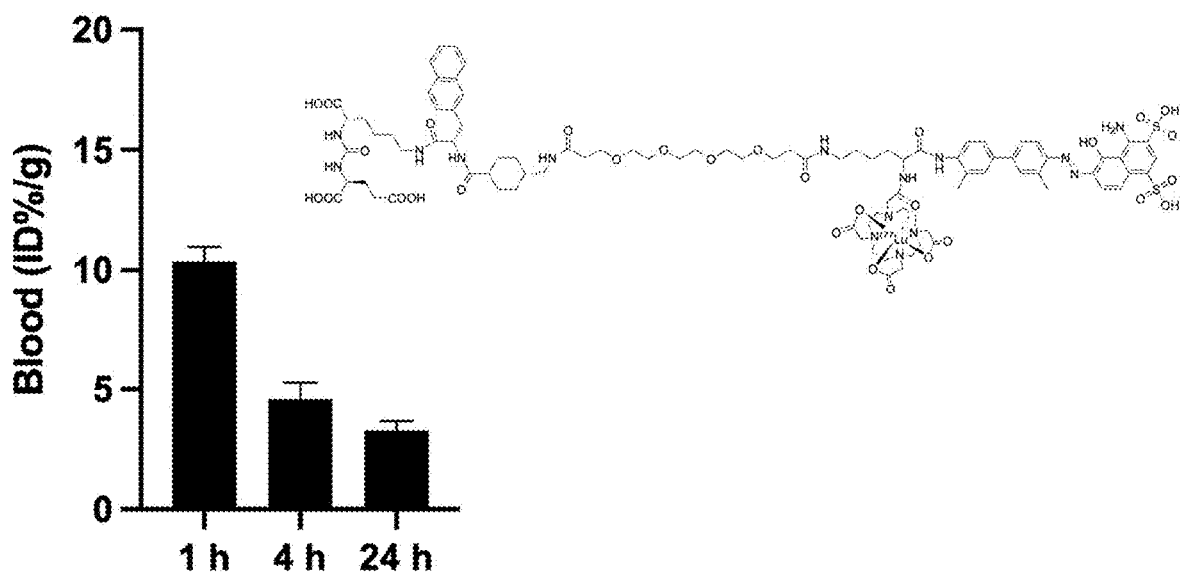

FIG. 7 shows uptake results in the blood of normal mice at different time points after $^{177}$Lu labeled compound (II-2) is injected.

Figure 8:
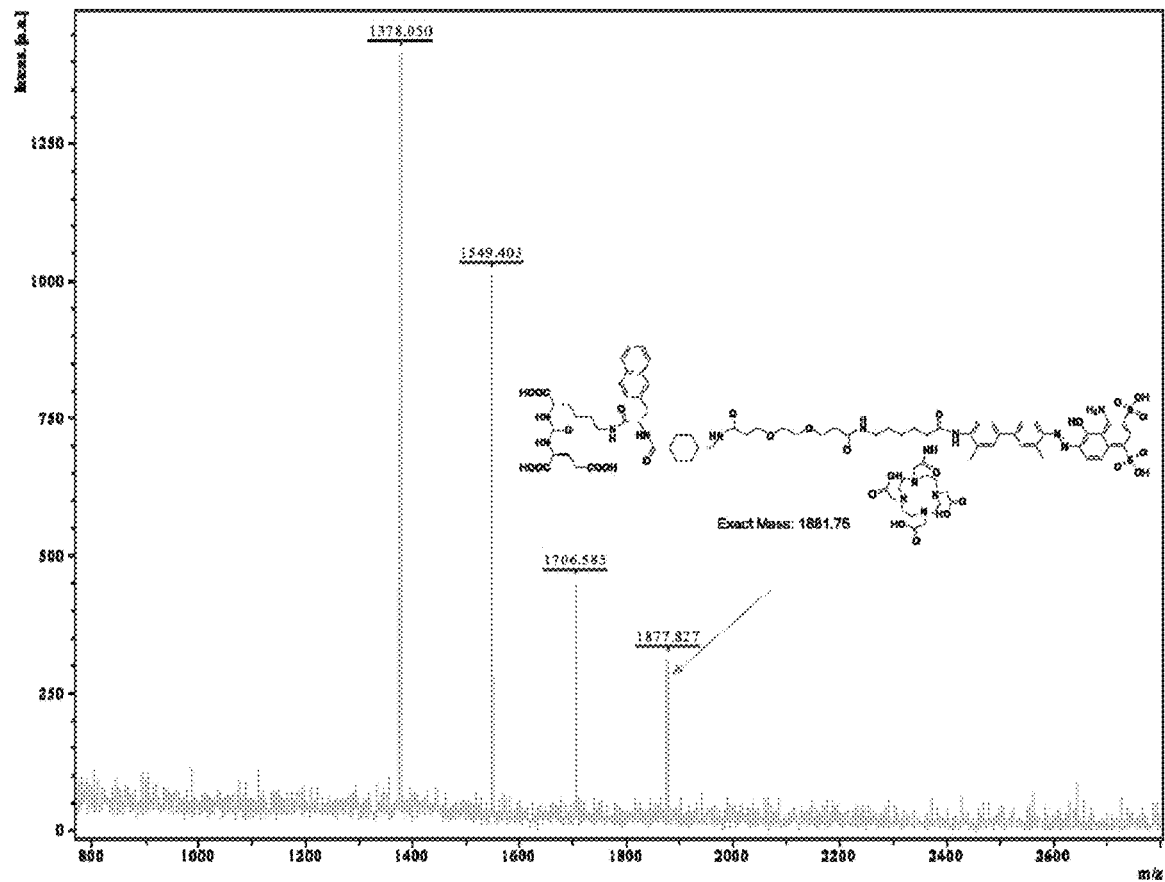

FIG. 8 is a diagram showing the mass spectrum of compound 10 prepared in Example 1.

Figure 9:
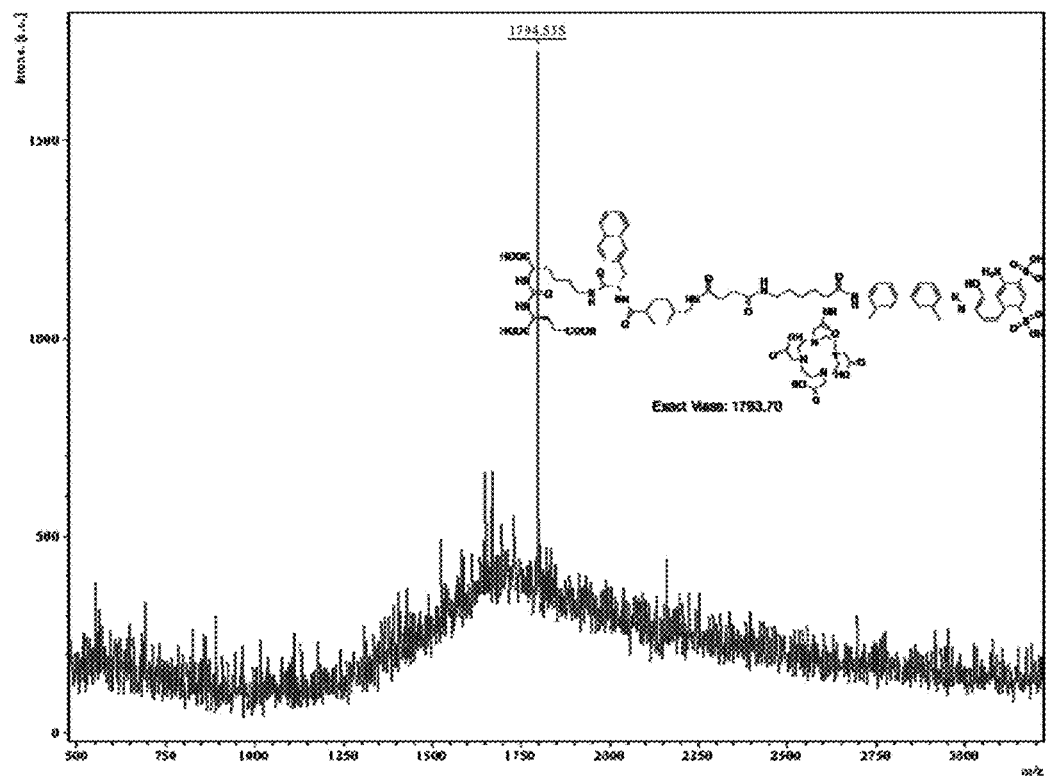

FIG. 9 is a diagram showing the mass spectrum of compound (II-3) prepared in Example 3.

Figure 10:
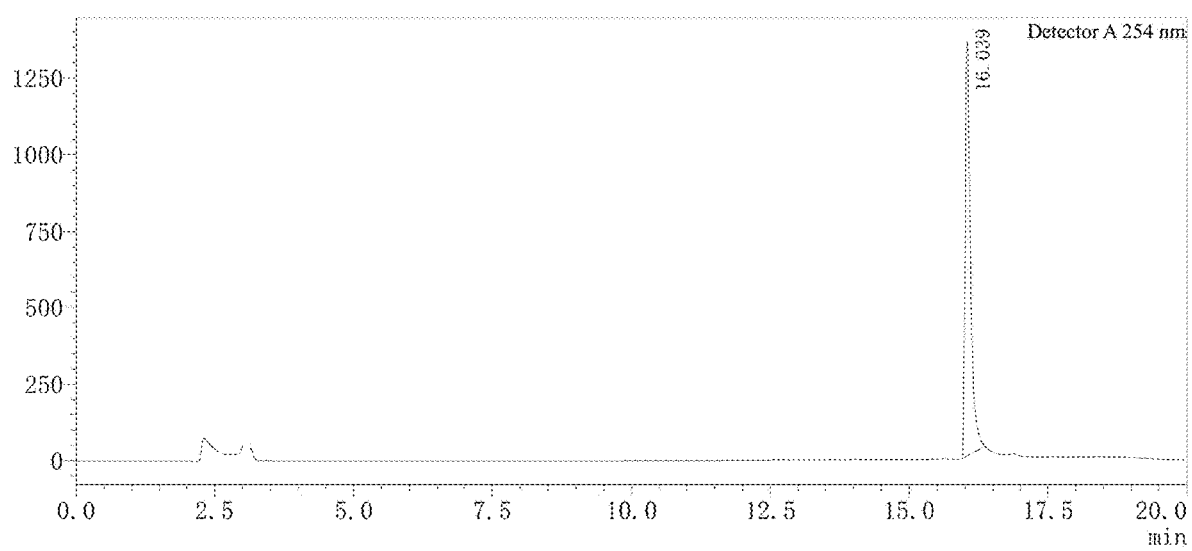

FIG. 10 is an HPLC chromatogram of compound 5 prepared in Example 1.

Figure 11:
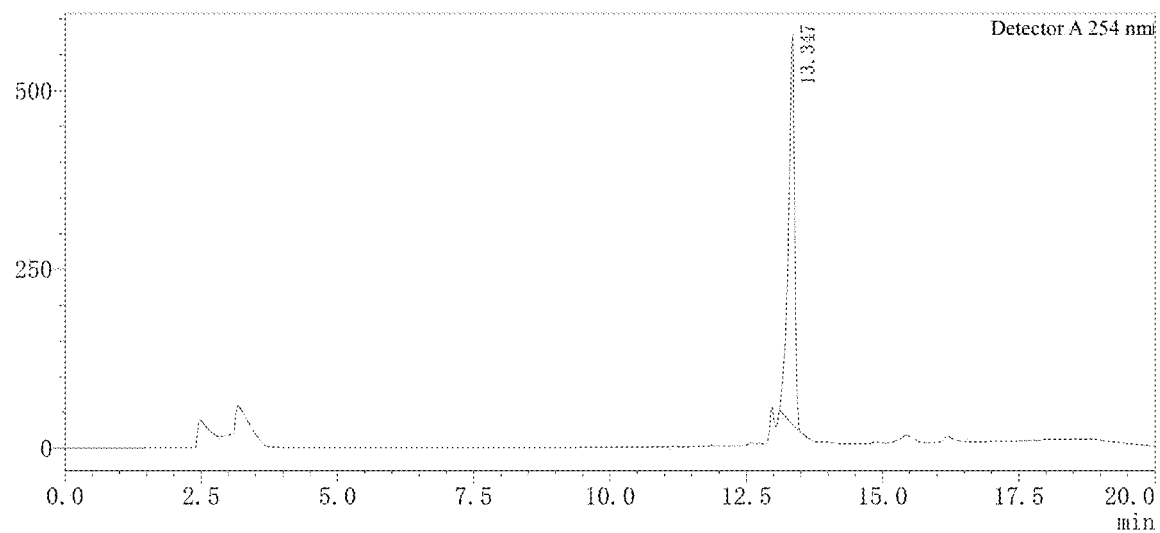

FIG. 11 is an HPLC chromatogram of compound 6 prepared in Example 1.

Figure 12:
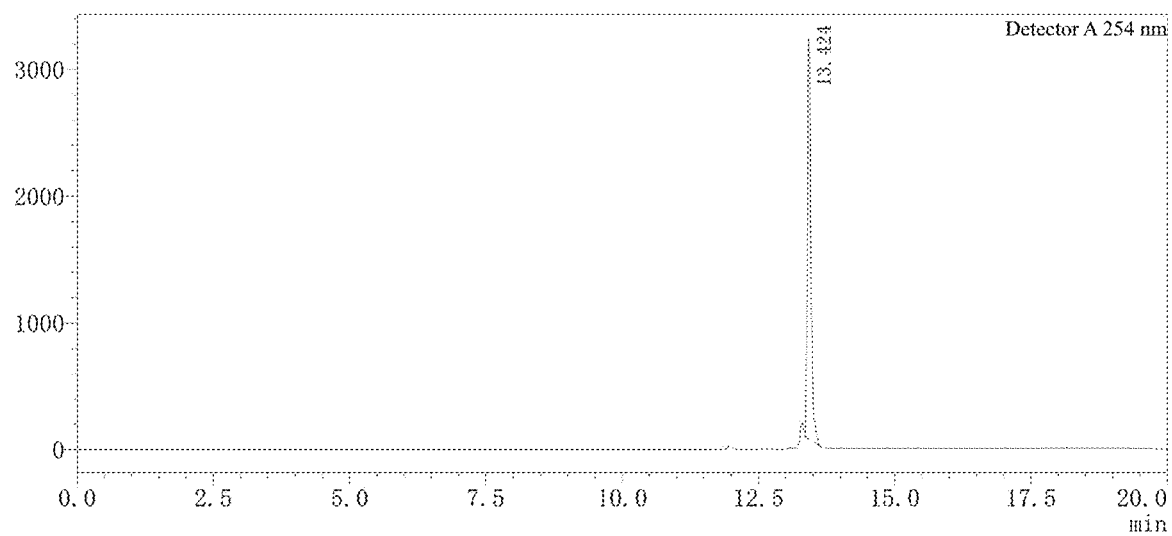

FIG. 12 is an HPLC chromatogram of compound 7 prepared in Example 1.

Figure 13:
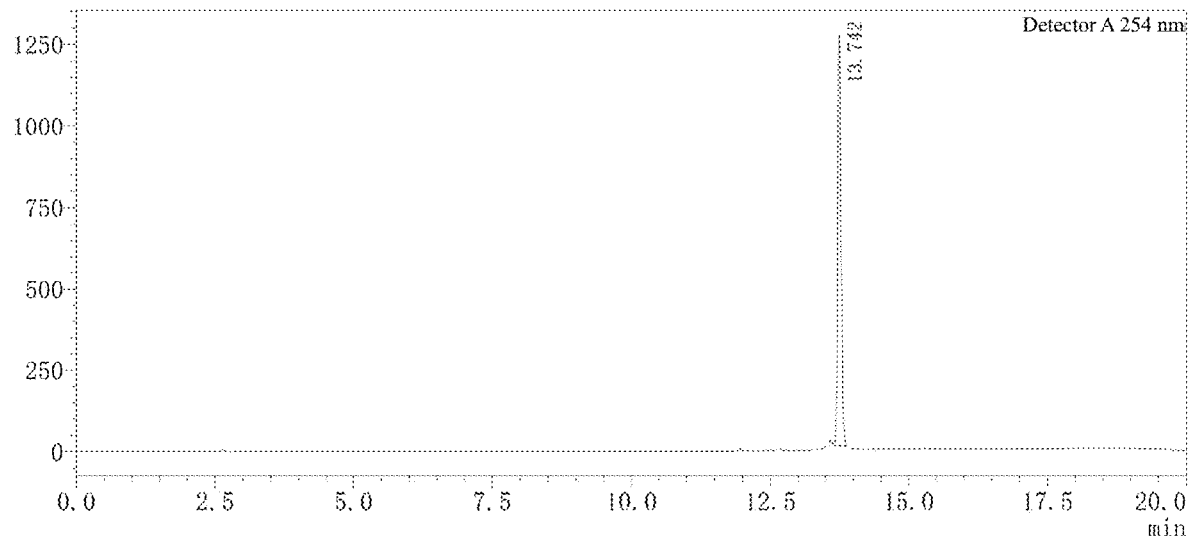

FIG. 13 is an HPLC chromatogram of compound 8 prepared in Example 1.

Figure 14:
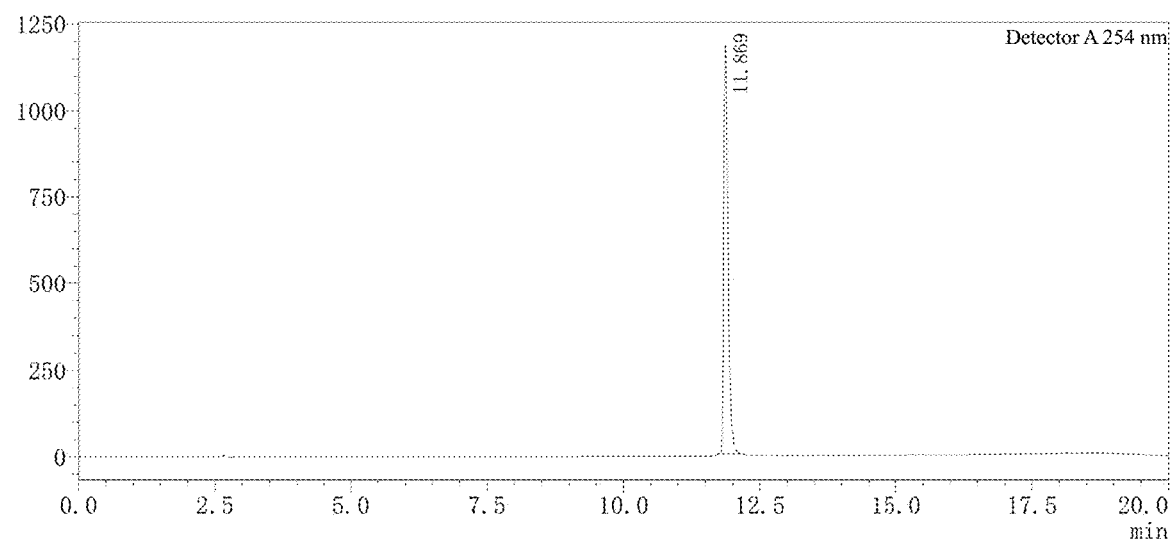

FIG. 14 is an HPLC chromatogram of compound 9 prepared in Example 1.

Figure 15:
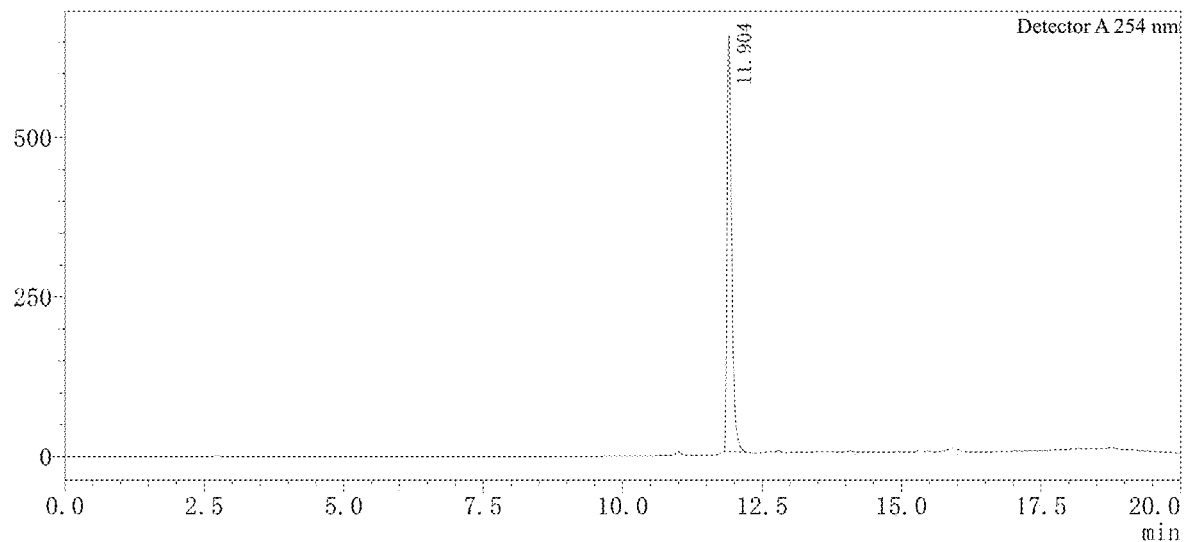

FIG. 15 is an HPLC chromatogram of compound 10 prepared in Example 1.

DETAILED DESCRIPTION OF EMBODIMENTS

Technical solutions of the present disclosure are further explained and described below in conjunction with specific embodiments and attached drawings.

Example 1: Preparation of Compound 10 Shown in Formula (II-1)

Synthesis of Compound 2

4,4'-diamino-3,3'-dimethyl biphenyl (compound 11) (2.12 g, 10.0 mmol), di-tert-butyl dicarbonate (2.2 g, 10.0 mmol), N,N-diisopropylethylamine (1.3 g, 10.0 mmol) and 20 mL of dichloromethane were separately put into a 100 mL flask, and stirred overnight at room temperature. After monitoring by HPLC that a reaction was completed (r.t. was 10.13 min), reduced pressure distillation was conducted to remove the solvent to obtain a crude product. Then purification was conducted with a silica gel column (a ratio of petroleum ether to ethyl acetate was 5:1) to obtain white solid compound 2 with a yield of 59%.

Synthesis of Compound 3

The compound 2 (0.31 g, 1.0 mmol) and 4 mL of acetonitrile were separately put into 50 mL flask in ice bath, 1.5 mL of 2 M hydrochloric acid was added dropwise to the reaction flask for a reaction for 15 min, and sodium nitrite (0.068 g, 1.0 mmol) was added to 2 mL of water for dissolution and then added dropwise to the reaction flask for a reaction for half an hour to obtain solution A for later use. 4,6-diamino-5-hydroxy-1,3-naphthalenedisulfonic acid (0.33 g, 1.0 mmol), sodium carbonate (0.105 g, 1.0 mmol) and 5 mL of water were added to another 50 mL reaction flask in ice bath to obtain solution B, and the solution A was slowly added dropwise to the solution B and stirred for a reaction for 2 h in the ice bath. Then purification was conducted with a reversed phase column, followed by freeze-drying to obtain pure compound 3 with yield of 47%.

Synthesis of a Compound 4

The compound 3 (0.52 g, 1.0 mmol) was dissolved in trifluoroacetic acid in ice bath. The system was heated to room temperature for a reaction for 2 h, and after the reaction was completed, reduced pressure distillation was conducted to remove the solvent to obtain a crude product. Then purification was conducted on the crude product with a reversed phase column, followed by freeze-drying to obtain pure compound 4 with yield of 73%.

Synthesis of a Compound 5

The compound 4 (0.54 g, 1.0 mmol), Nα-Fmoc-Nε-Boc-L-lysine (0.46 g, 1.0 mmol), HATU (0.38 g, 1.0 mmol), N,N-diisopropylethylamine (0.26 g, 2.0 mmol) and 10 mL of N,N-dimethylformamide were separately put into 100 mL flask. A reaction mixture was stirred until a reaction was completed, and reduced pressure distillation was conducted to remove the solvent to obtain a crude product. Then purification was conducted on the crude product with a reversed phase column, followed by freeze-drying to obtain pure compound 5 with yield of 57%.

Synthesis of a Compound 6

Tert-butyl and Boc protective groups were removed from compound 5 using a mixture of thioanisole, 1,2-ethanedithiol, anisole and TFA (at ratio of 5:3:2:90) at room temperature to obtain compound 6. After a reaction was completed, the TFA was removed by an argon flow, and the resulting product was dissolved in 10 mL of N,N-dimethylformamide for later use.

Synthesis of Compound 7

COOH-PEG$_2$-COOH (0.23 g, 1.10 mmol), HATU (0.38 g, 1.0 mmol) and N,N-diisopropylethylamine (0.39 g, 3.0 mmol) were separately added to N,N-dimethylformamide solution of the compound 6. The system was stirred overnight at room temperature, and a reaction was completed according to monitoring by HPLC (r.t. was 10.84 min). Reduced pressure distillation was conducted to remove the solvent to obtain a crude product. Then purification was conducted on the crude product with a reversed phase column, followed by freeze-drying to obtain pure compound 7 with yield of 50% in two steps.

Synthesis of a Compound 8

The compound 7 (0.21 g, 0.2 mmol), 1-(3-dimethylaminopropyl)-3-ethylcarbodiimide hydrochloride (0.04 g, 0.2 mmol), NHS (0.02 g, 0.2 mmol) and 10 mL of N,N-dimethylformamide were separately put into 50 mL flask. After a reaction was carried out for 4 h, N,N-diisopropylethylamine (0.06 g, 0.5 mmol) and PSMA-617 (0.13 g, 0.2 mmol) were added. A reaction mixture was stirred for a reaction, and the reaction was completed according to monitoring by HPLC (r.t. was 12.16 min). Reduced pressure distillation was conducted to remove the solvent to obtain a crude product. Then purification was conducted on the crude product with a reversed phase column, followed by freeze-drying to obtain pure compound 8 with yield of 59%.

Synthesis of a Compound 9

The compound 8 (0.16 g, 0.1 mmol) and piperidine (0.08 g, 10.0 mmol) were separately put into 5 mL of DMF in 25 mL flask. The process of removing protective groups was monitored by HPLC until a reaction was completed (r.t. was 10.47 min). Reduced pressure distillation was conducted to remove the solvent to obtain a crude product. Then purification was conducted on the crude product with a reversed phase column, followed by freeze-drying to obtain pure compound 9 with yield of 63%.

Synthesis of a Compound 10

The compound 9 (0.13 g, 0.1 mmol), DOTA-NHS (0.05 g, 0.1 mmol) and N,N-diisopropylethylamine (0.04 g, 0.3 mmol) were sequentially put into 5 mL of N,N-dimethylformamide in 25 mL flask. The reaction system was stirred for a reaction at room temperature, and the process of removing protective groups was monitored by HPLC until the reaction was completed (r.t. was 11.35 min). Reduced pressure distillation was conducted to remove the solvent to obtain a crude product. Then purification was conducted on the crude product with a reversed phase column, followed by freeze-drying to obtain pure compound 10 with yield of 61%. Characterization of the structure of the resulting compound is shown in FIG. 8.

A Synthesis Route in the Above Steps is as Follows

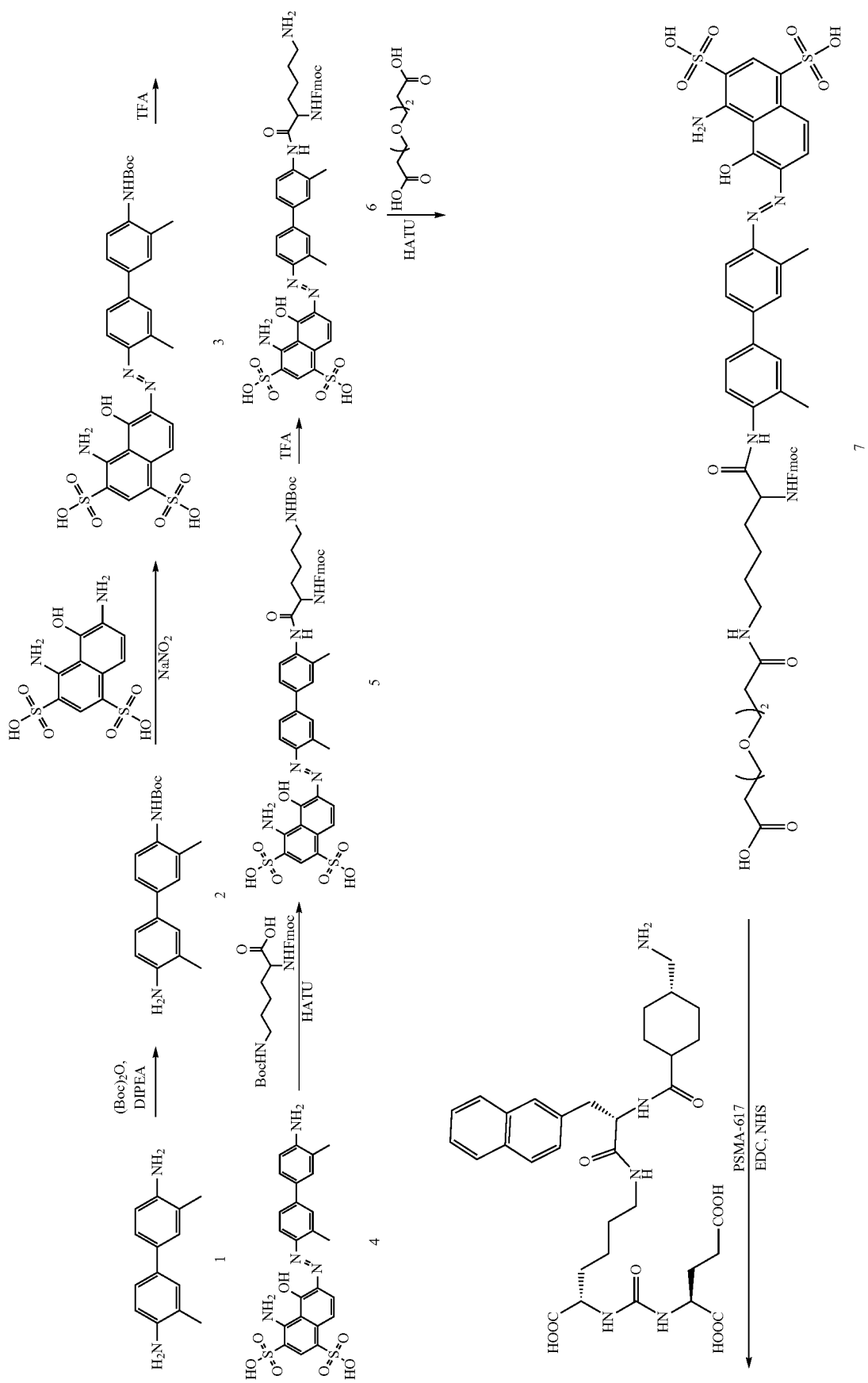

-continued
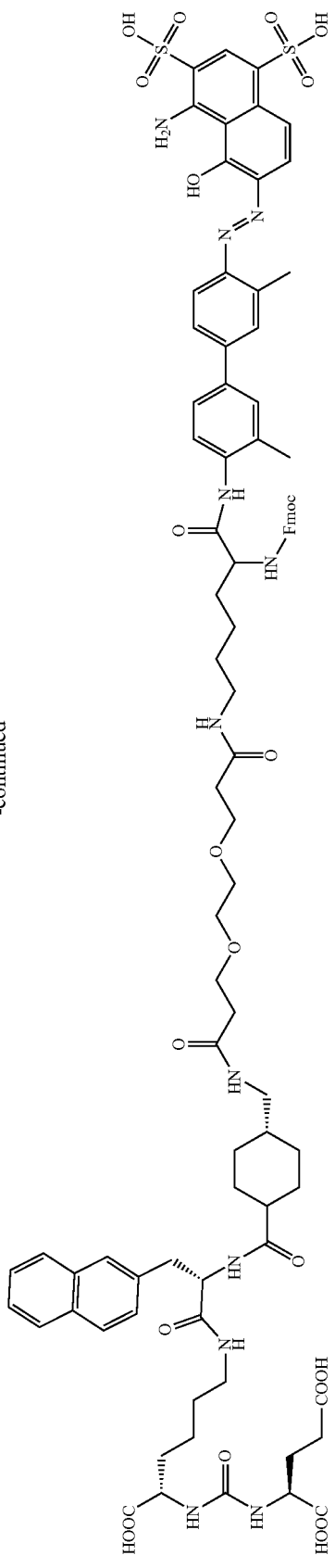
8
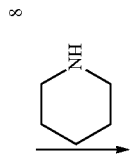
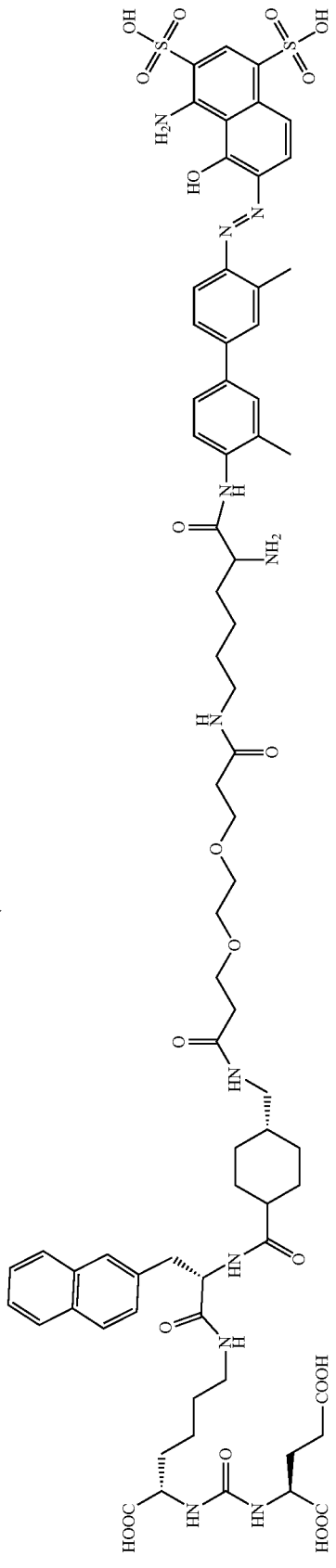
9
DOTA-NHS, DIPEA

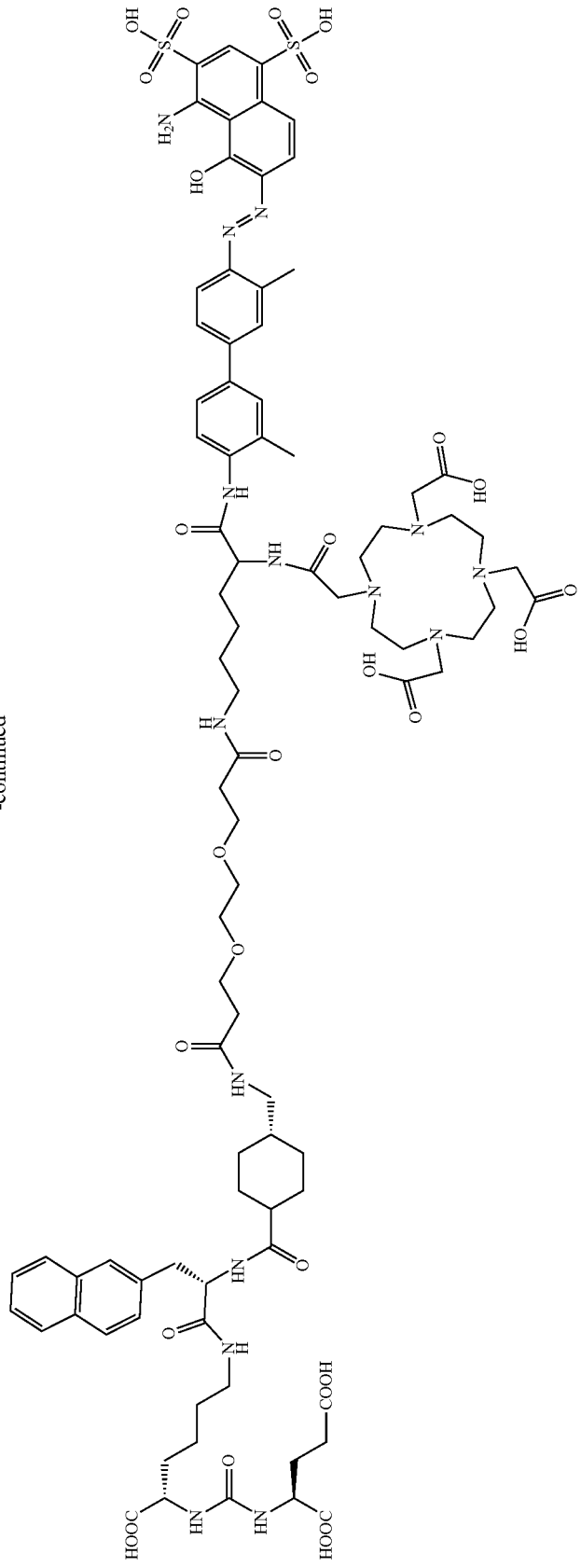

Examples 2- Examples 6

Compounds in Examples 2-Examples 6 have structures shown in Formula (II-2) to Formula (II-6) respectively, and preparation methods of the compounds can refer to the preparation method in Example 1. For example, the COOH-PEG$_2$-COOH reacting with the compound 6 in Example 1 was substituted with COOH-PEG$_4$-COOH, malonic acid or other suitable compounds for preparation of the compounds shown in Formula (II-2) and Formula (II-3). The Nα-Fmoc-Nε-Boc-L-lysine reacting with the compound 4 in Example 1 was substituted with Boc-glycine for preparation of the compounds shown in Formula (II-4) to Formula (II-6), or the PSMA-617 reacting with the compound 7 in Example 1 was substituted with PSMA-617-(Fmoc)Lys- to obtain corresponding structures as follows:

Formula (II-2)
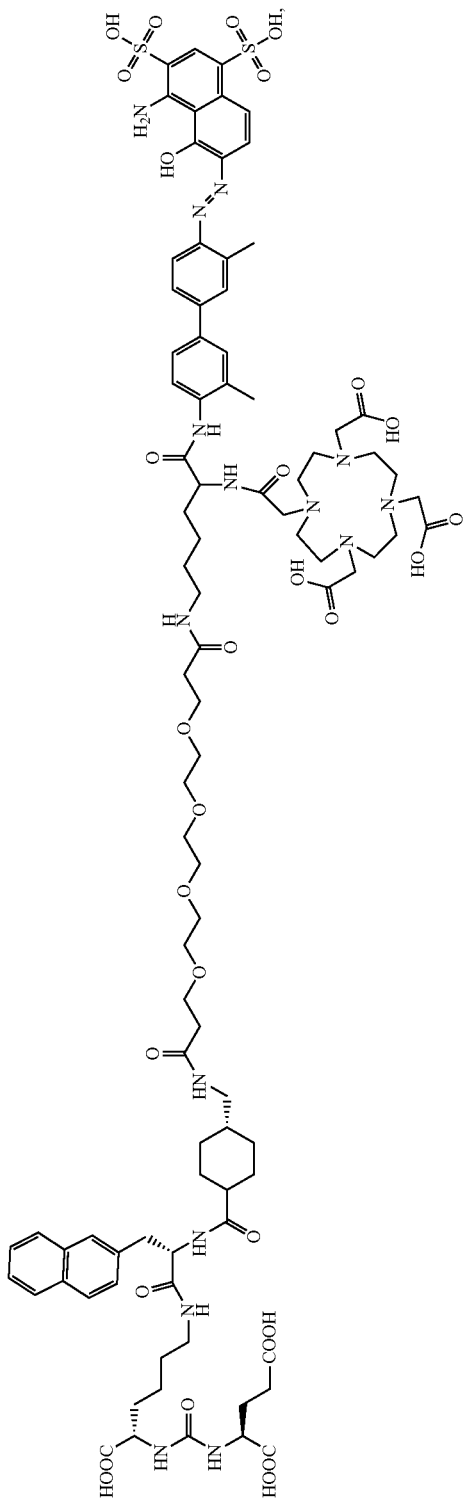

-continued
Formula (II-3)
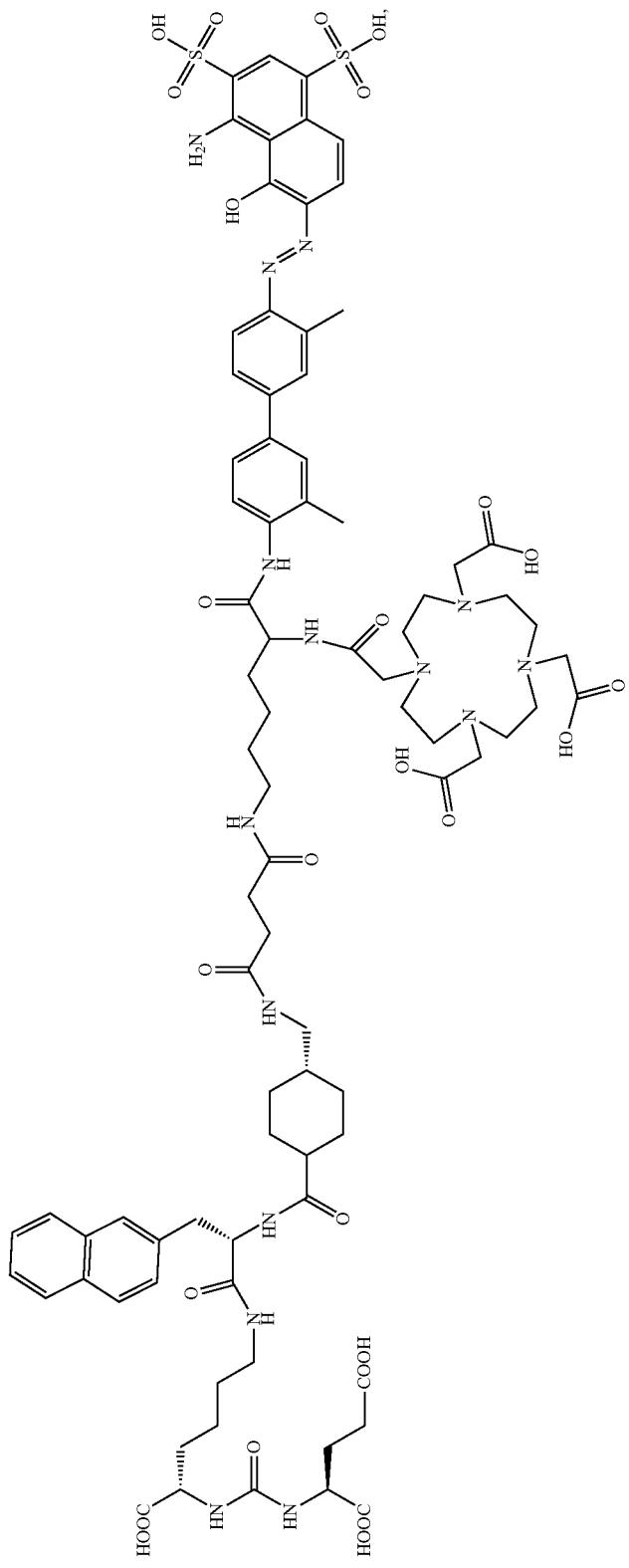
Formula (II-4)
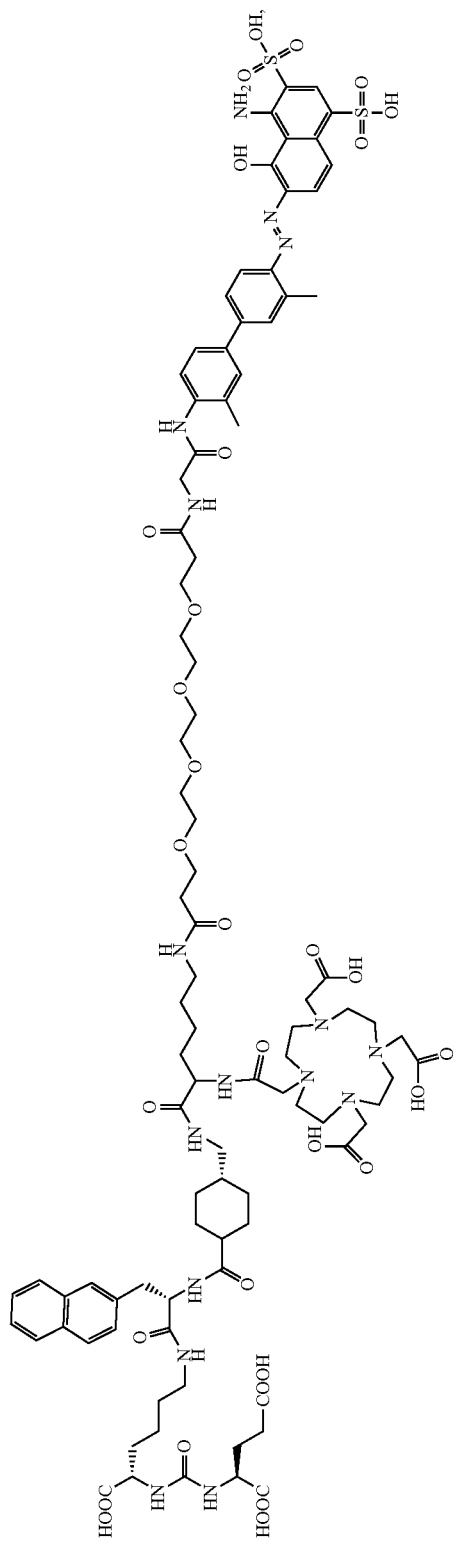

-continued
Formula (II-5)
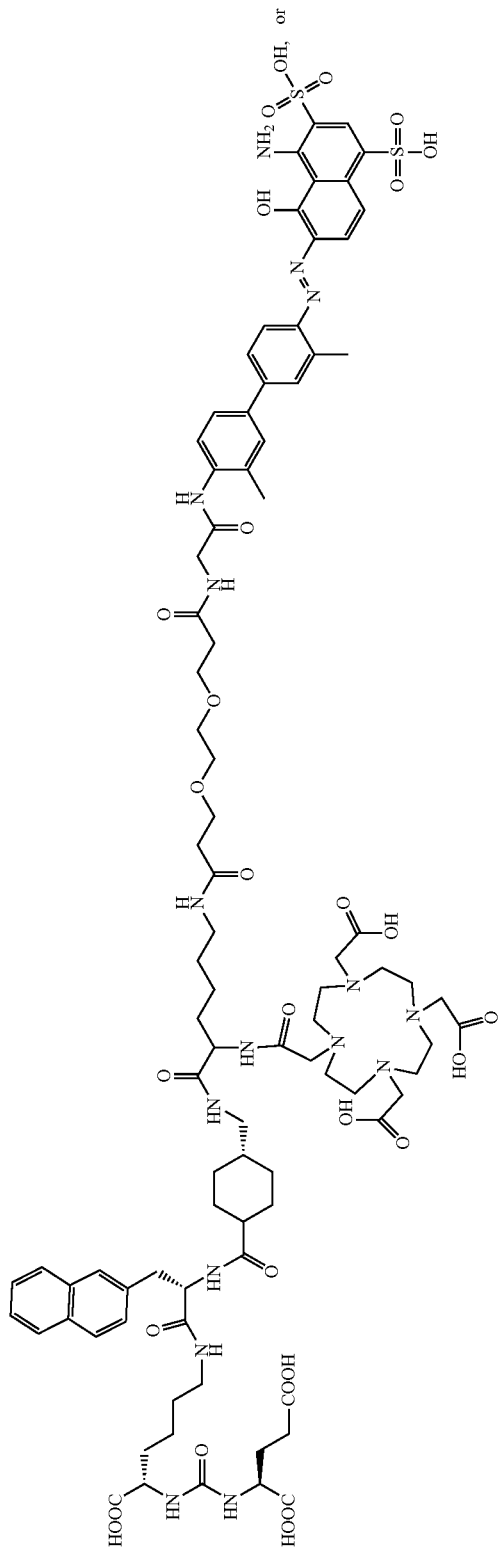
or
Formula (II-6)
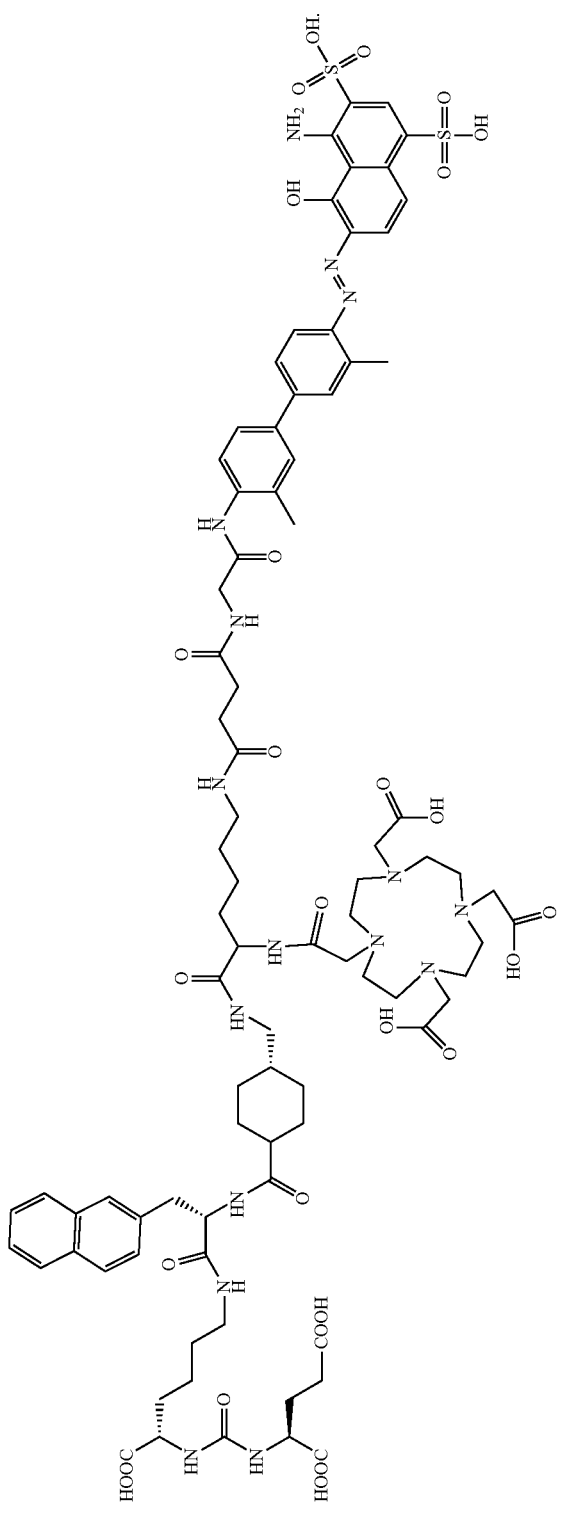

Characterization of the structure of the compound (II-3) is shown in FIG. 9.

Examples 7- Examples 30

With reference to the preparation methods in Examples 1- Examples 6, compound shown in the following Formula (I) was prepared.

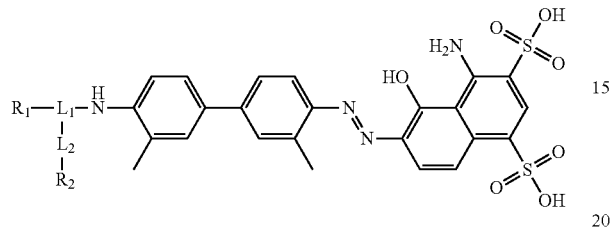

Formula (I)

| Example number | R1 | R2 |
|---|---|---|
| 7 | HOOC-...HN-C(=O)-NH-(CH2)-C(=O)-NH-(CH2)4-NH- with HOOC-CH2-COOH branch | NOTA-like macrocycle with carboxylates |
| 8 | (same as 7) | DTPA-like open chain with HOOC groups |
| 9 | (same as 7) | DOTA-like macrocycle with carboxylates |
| 10 | (same as 7) | DFO-NCS (desferrioxamine-isothiocyanate) |
| 11 | (same as 7) | DOTA macrocycle |
| 12 | (same as 7) | DOTA macrocycle |

-continued
| | | |
|---|---|---|
| 13 | 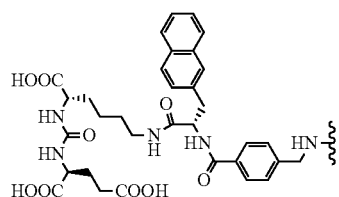 [SMILES: *NCc1ccc(C(=O)N[C@@H](Cc2ccc3ccccc3c2)C(=O)NCCCC[C@H](NC(=O)N[C@@H](CCC(=O)O)C(=O)O)C(=O)O)cc1] | 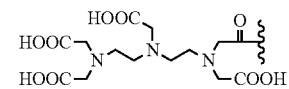 |
| 14 | 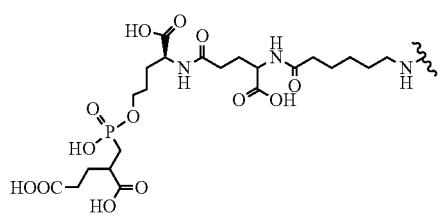 [SMILES: *NCCCCCC(=O)NC(CCC(=O)N[C@@H](CCCOP(=O)(O)CC(CCC(=O)O)C(=O)O)C(=O)O)C(=O)O] | 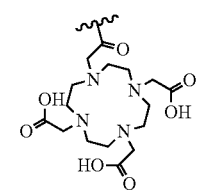 [SMILES: *C(=O)CN1CCN(CC(=O)O)CCN(CC(=O)O)CCN(CC(=O)O)CC1] |
| 15 | 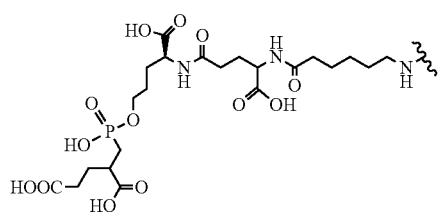 [SMILES: *NCCCCCC(=O)NC(CCC(=O)N[C@@H](CCCOP(=O)(O)CC(CCC(=O)O)C(=O)O)C(=O)O)C(=O)O] | 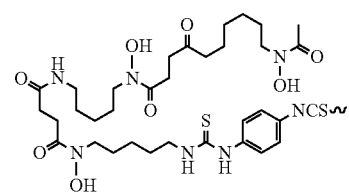 |
| 16 | 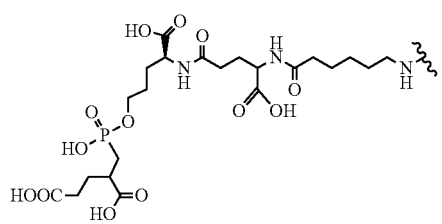 [SMILES: *NCCCCCC(=O)NC(CCC(=O)N[C@@H](CCCOP(=O)(O)CC(CCC(=O)O)C(=O)O)C(=O)O)C(=O)O] | 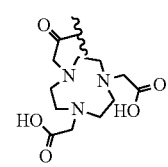 |
| 17 | 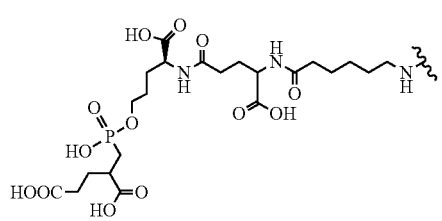 [SMILES: *NCCCCCC(=O)NC(CCC(=O)N[C@@H](CCCOP(=O)(O)CC(CCC(=O)O)C(=O)O)C(=O)O)C(=O)O] | 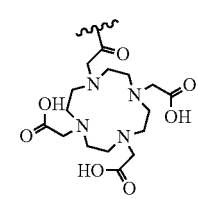 [SMILES: *C(=O)CN1CCN(CC(=O)O)CCN(CC(=O)O)CCN(CC(=O)O)CC1] |
| 18 | 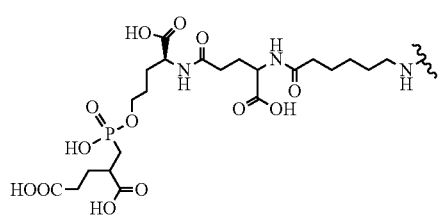 [SMILES: *NCCCCCC(=O)NC(CCC(=O)N[C@@H](CCCOP(=O)(O)CC(CCC(=O)O)C(=O)O)C(=O)O)C(=O)O] | 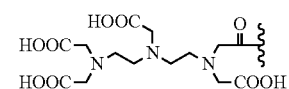 |
| 19 | 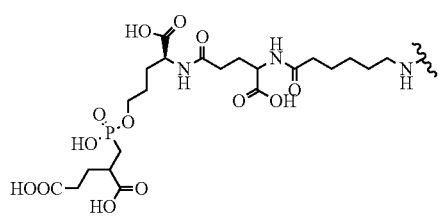 [SMILES: *NCCCCCC(=O)NC(CCC(=O)N[C@@H](CCCOP(=O)(O)CC(CCC(=O)O)C(=O)O)C(=O)O)C(=O)O] | 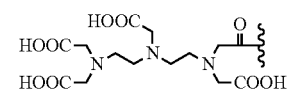 |

-continued
| | 51 | 52 |
|---|---|---|
| 20 | 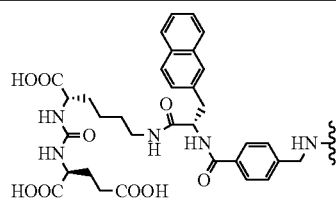 | 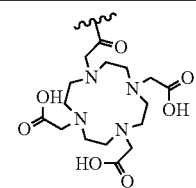 |
| 21 | 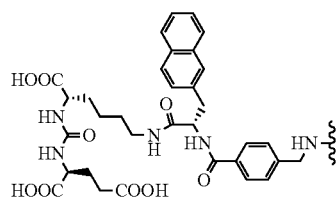 [SMILES: *NCc1ccc(C(=O)N[C@@H](Cc2ccc3ccccc3c2)C(=O)NCCCC[C@H](NC(=O)N[C@@H](CCC(=O)O)C(=O)O)C(=O)O)cc1] | 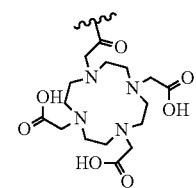 [SMILES: *C(=O)CN1CCN(CC(=O)O)CCN(CC(=O)O)CCN(CC(=O)O)CC1] |
| 22 | 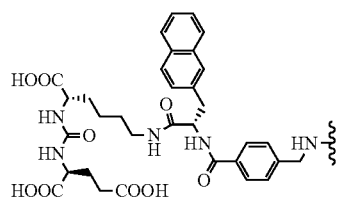 [SMILES: *NCc1ccc(C(=O)N[C@@H](Cc2ccc3ccccc3c2)C(=O)NCCCC[C@H](NC(=O)N[C@@H](CCC(=O)O)C(=O)O)C(=O)O)cc1] | 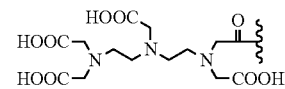 |
| 23 | 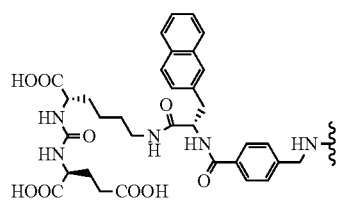 [SMILES: *NCc1ccc(C(=O)N[C@@H](Cc2ccc3ccccc3c2)C(=O)NCCCC[C@H](NC(=O)N[C@@H](CCC(=O)O)C(=O)O)C(=O)O)cc1] | 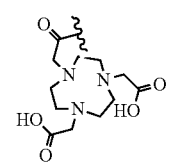 |
| 24 | 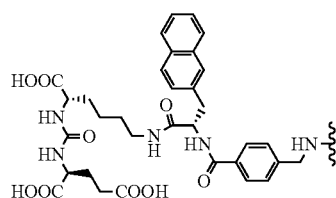 [SMILES: *NCc1ccc(C(=O)N[C@@H](Cc2ccc3ccccc3c2)C(=O)NCCCC[C@H](NC(=O)N[C@@H](CCC(=O)O)C(=O)O)C(=O)O)cc1] | 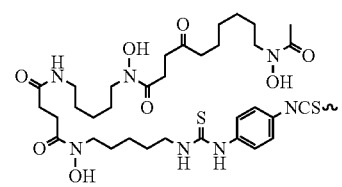 |
| 25 | 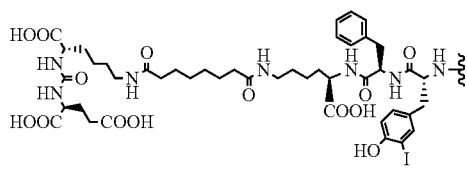 [SMILES: *N[C@H](Cc1ccc(O)c(I)c1)C(=O)N[C@H](Cc1ccccc1)C(=O)N[C@H](CCCCNC(=O)CCCCCCC(=O)NCCCC[C@H](NC(=O)N[C@@H](CCC(=O)O)C(=O)O)C(=O)O)C(=O)O] | 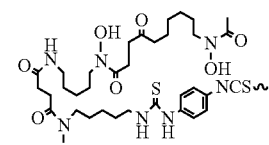 |
| 26 | 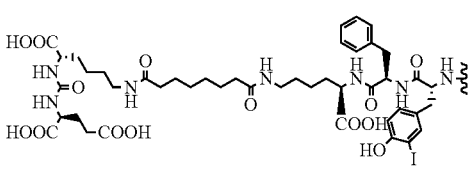 [SMILES: *N[C@H](Cc1ccc(O)c(I)c1)C(=O)N[C@H](Cc1ccccc1)C(=O)N[C@H](CCCCNC(=O)CCCCCCC(=O)NCCCC[C@H](NC(=O)N[C@@H](CCC(=O)O)C(=O)O)C(=O)O)C(=O)O] | 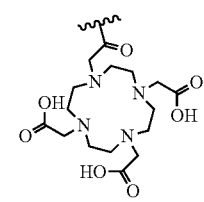 [SMILES: *C(=O)CN1CCN(CC(=O)O)CCN(CC(=O)O)CCN(CC(=O)O)CC1] |
| 27 | 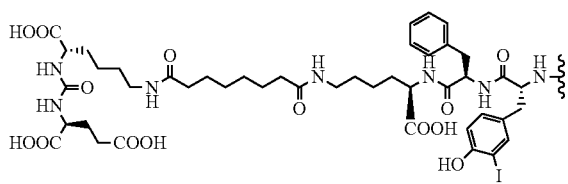 [SMILES: *N[C@H](Cc1ccc(O)c(I)c1)C(=O)N[C@H](Cc1ccccc1)C(=O)N[C@H](CCCCNC(=O)CCCCCCC(=O)NCCCC[C@H](NC(=O)N[C@@H](CCC(=O)O)C(=O)O)C(=O)O)C(=O)O] | 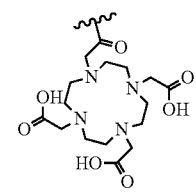 [SMILES: *C(=O)CN1CCN(CC(=O)O)CCN(CC(=O)O)CCN(CC(=O)O)CC1] |

-continued
| | | |
|---|---|---|
| 28 | 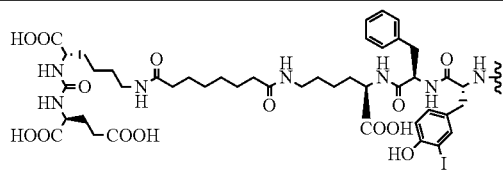 | 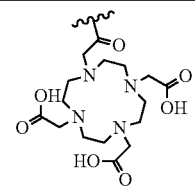 |
| 29 | 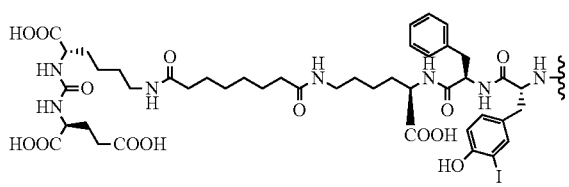 [SMILES: *N[C@H](Cc1ccc(O)c(I)c1)C(=O)N[C@H](Cc1ccccc1)C(=O)N[C@H](CCCCNC(=O)CCCCCCC(=O)NCCCC[C@H](NC(=O)N[C@@H](CCC(=O)O)C(=O)O)C(=O)O)C(=O)O] | 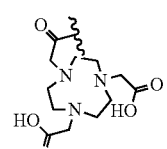 |
| 30 | 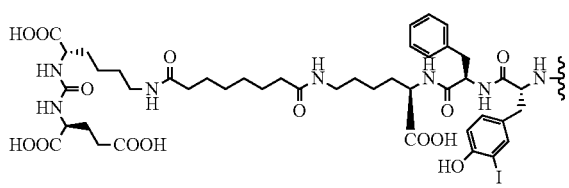 [SMILES: *N[C@H](Cc1ccc(O)c(I)c1)C(=O)N[C@H](Cc1ccccc1)C(=O)N[C@H](CCCCNC(=O)CCCCCCC(=O)NCCCC[C@H](NC(=O)N[C@@H](CCC(=O)O)C(=O)O)C(=O)O)C(=O)O] | 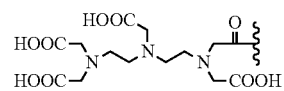 |
| Example number | L1 | L2 |
|---|---|---|
| 7 | 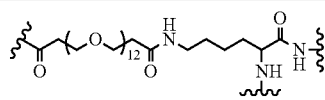 |  |
| 8 | 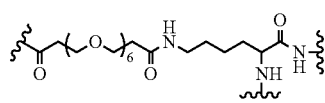 | 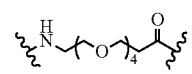 |
| 9 | 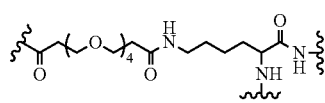 | 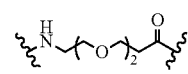 |
| 10 | 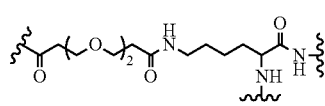 | 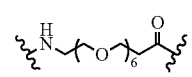 |
| 11 | 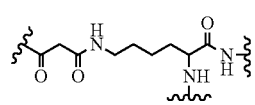 | 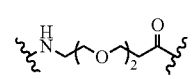 |
| 12 | 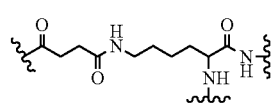 [SMILES: *NC(=O)C(CCCCNC(=O)CCC(*)=O)N*] | 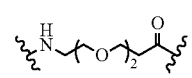 |
| 13 | 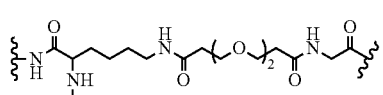 | — |
| 14 | 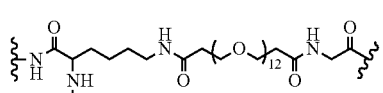 | 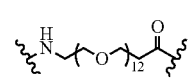 |
| 15 | 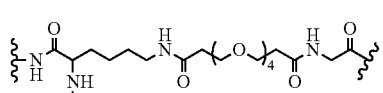 | 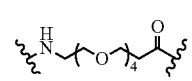 |

-continued
| | | |
|---|---|---|
| 16 | 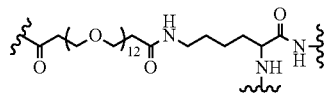 | 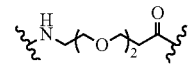 |
| 17 | 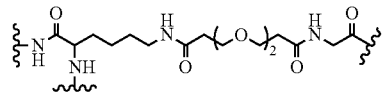 | 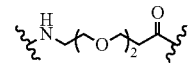 |
| 18 | 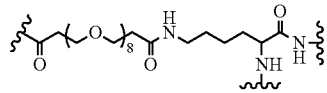 | — |
| 19 | 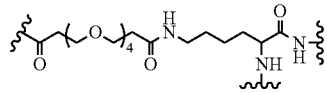 | 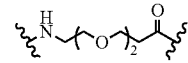 |
| 20 | 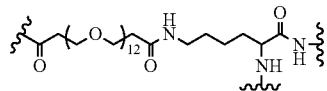 | 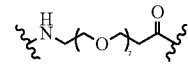 |
| 21 | 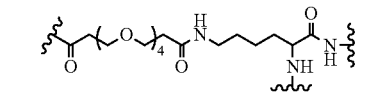 | 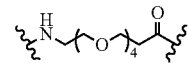 |
| 22 | 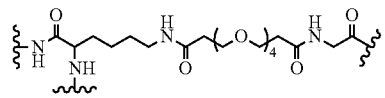 | 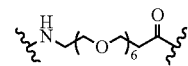 |
| 23 | 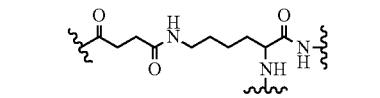 [SMILES: *NC(=O)C(CCCCNC(=O)CCC(*)=O)N*] | 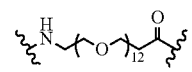 |
| 24 | 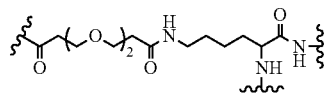 | — |
| 25 | 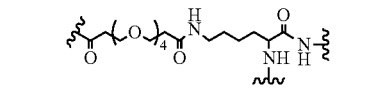 | 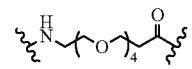 |
| 26 | 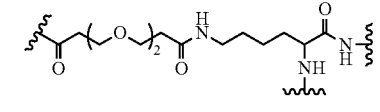 | 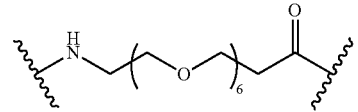 |
| 27 | 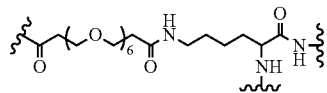 | — |
| 28 | 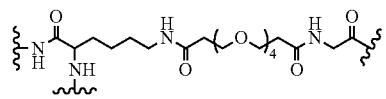 | 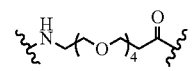 |
| 29 | 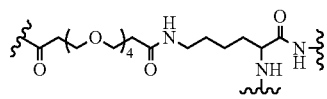 | — |

| 30 | 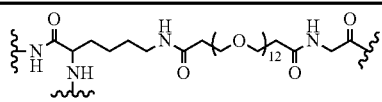 | 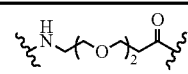 |
|---|---|---|

Example 31: Preparation of $^{177}$Lu Labeled Complex

Wet method: Sodium acetate solution of about 18.5-1,850 MBq of $^{177}$LuCl$_3$ was added to acetic acid-acetate solution (1.0 g/L) containing 0.5 mL of the compound 10 in Example 1 in a centrifuge tube, and a reaction was carried out at 90° C. for 20 min. A small C18 separation column was slowly rinsed with 10 mL of anhydrous ethanol first, and then rinsed with 10 mL of water. Resulting in labeled solution was diluted with 10 mL of water, and then sampled to the separation column. Unlabeled $^{177}$Lu ions were removed with 10 mL of water, and rinsing was conducted with 0.3 mL of a 10 mM ethanol solution of HCl to obtain $^{177}$Lu labeled complex. The rinsed solution was diluted with normal saline, followed by aseptic filtration to obtain injection of the $^{177}$Lu labeled complex.

Freeze-drying method: Sodium acetate solution of about 18.5-1,850 MBq if $^{177}$LuCl$_3$ was added to a freeze-dried medicine box containing the compound 10 in Example 1, and uniformly mixed for a reaction at 90° C. for 20 min. A small C18 separation column was slowly rinsed with 10 mL of anhydrous ethanol first, and then rinsed with 10 mL of water. Resulting labeled solution was diluted with 10 mL of water, and then sampled to the separation column. Unlabeled $^{177}$Lu ions were removed with 10 mL of water, and rinsing was conducted with 0.3 mL of 10 mM ethanol solution of HCl to obtain rinsed solution of $^{177}$Lu labeled complex. The rinsed solution was diluted with normal saline, followed by aseptic filtration to obtain injection of the $^{177}$Lu labeled complex.

Experimental Example: Analysis and Application Effect

1. HPLC Analysis and Identification

An HPLC system was as follows: SHIMADZULC-20A; and a C18 chromatographic column (YMC, 3 μm, 4.6*150 mm) was used for analysis. Detection was conducted at wavelength of 254 nm and flow rate of 1 mL/min according to the following rinsing gradient: at 0-3 min, 10% of acetonitrile and 90% of water (50 mM ammonium acetate) were remained unchanged; at 3-16 min, the system was increased to include 90% of acetonitrile and 10% of water (50 mM ammonium acetate); at 16-18 min, 90% of acetonitrile and 10% of water (50 mM ammonium acetate) were remained; at 18-20 min, the system was reduced to include 10% of acetonitrile and 90% of water (50 mM ammonium acetate); and at 20-22 min, 10% of acetonitrile and 90% of water (50 mM ammonium acetate) were retained.

Compound 5, compound 6, compound 7, compound 8, compound 9 and compound 10 in Example 1 were identified and analyzed according to the above system. Identification and analysis results are shown in FIG. 10, FIG. 11, FIG. 12, FIG. 13, FIG. 14 and FIG. 15, respectively.

The radiolabeled probe prepared in Example 31 is used as an experimental agent below, and experiments for determining properties of the probe are described as follows.

2. Uptake Experiment of $^{177}$Lu Labeled Complex in Subcutaneous Transplanted Tumor Model Mice with Prostate Cancer The compound in Example 31 or another prior radioactive probe targeting PSMA was injected into subcutaneous transplanted tumor model mice with prostate cancer, and uptake results in tumors and distribution results in tissues were compared. A specific plan is as follows.

The subcutaneous transplanted tumor model mice with prostate cancer (22RV1) were randomly divided into 3 groups including an experimental group, a control group A and a control group B with 3 mice in each group.

$^{77}$Lu complex with purity of greater than 95% was prepared according to the method in Example 31. The complex is obtained by labeling compound 10 in Example 1 with $^{177}$Lu, which was used as medicine B for the experimental group in the experiment.

$^{177}$Lu-PSMA 617 with purity of greater than 95% was prepared according to a prior method, which was used as medicine A for the control group A in the experiment.

$^{177}$Lu-EB-PSMA 617 with purity of greater than 95% was prepared according to the method in Example 8 in WO2019/165200, which was used as medicine C for the control group B in the experiment.

5 MBq of medicine B, the medicine A and the medicine C were intravenously injected into tails of the mice in the experimental group, the control group A and the control group B, respectively. After the injection was completed for 24 h, the mice in each group were sacrificed and dissected to obtain tumor tissues, blood or other tissues. The obtained tissues were weighed, and measured by a γ counter to obtain the radioactive counting of samples in the experimental group, the control group A and the control group B. Measured data were subtracted from the background, the decay time was corrected, and then average values were obtained. The data was expressed as the percentage of injected dose per gram tissue (% ID/g) of the dose uptake in tissues per gram in the injected dose. Results are shown in FIG. 1, FIG. 3 and FIG. 4.

Figure 1:
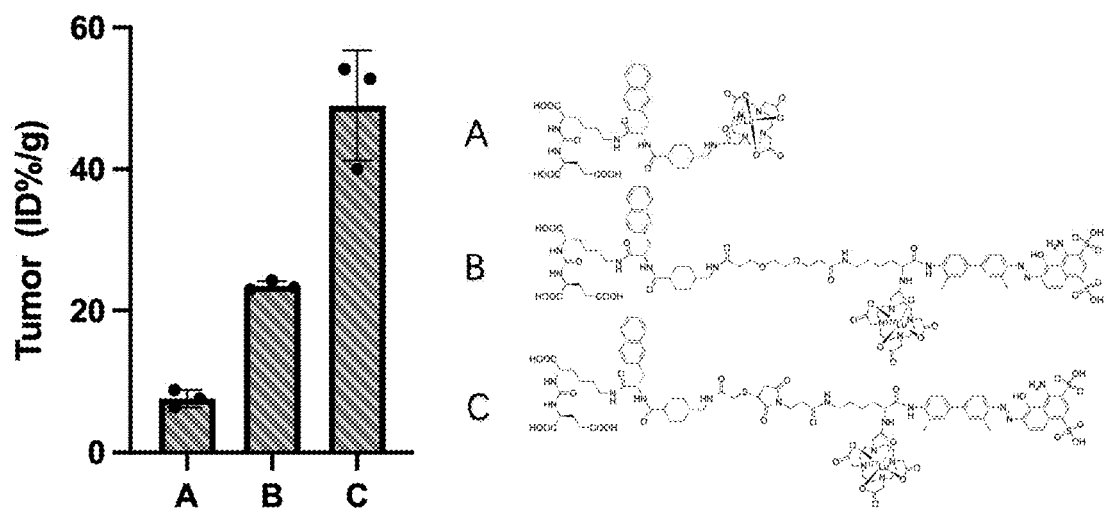
FIG. 1 shows uptake results in tumors 24 h after different medicines are injected into subcutaneous transplanted tumor model mice with prostate cancer.

From FIG. 1, it can be seen that the uptake in tumors after the $^{177}$Lu complex (B) in Example 31 of the present disclosure is injected for 24 h is 23.46±0.63% ID/g, which is much higher than that after the $^{177}$Lu-PSMA 617 (A) is injected in the control group A (7.60±1.22% ID/g) and lower than that after the $^{177}$Lu-EB-PSMA 617 (C) is injected in the control group B (48.97+7.77% ID/g).

Figure 3:
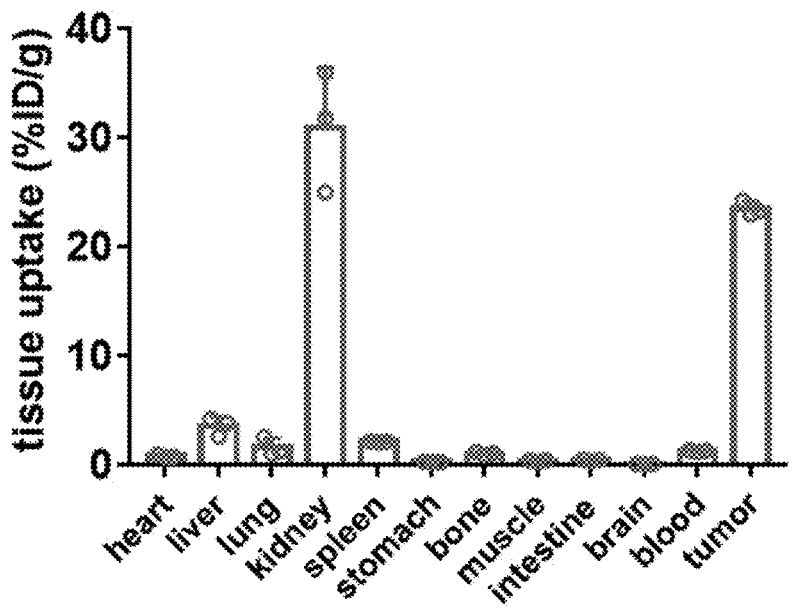
FIG. 3 shows distribution results in tissues 24 h after compound in Example 31 is injected into subcutaneous transplanted tumor model mice with prostate cancer.
Figure 4:
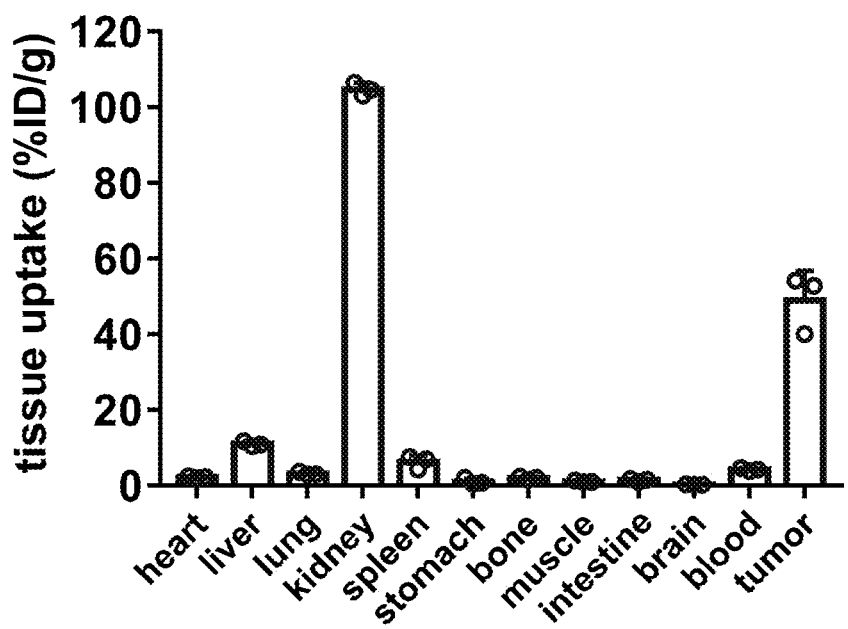
FIG. 4 shows distribution results in tissues 24 h after $^{177}$Lu-EB-PSMA 617 is injected into subcutaneous transplanted tumor model mice with prostate cancer.

FIG. 3 and FIG. 4 show the distribution of major tissues 24 h after the $^{177}$Lu complex (B) in Example 31 of the present disclosure is injected in the experimental group and the $^{177}$Lu-EB-PSMA 617 (C) is injected in the control group B, respectively. It can be observed that the uptake of the $^{177}$Lu complex in Example 31 of the present disclosure (FIG. 3) in the kidneys 24 h after the injection is much lower than that in the $^{177}$Lu-EB-PSMA-617 group (FIG. 4).

3. Experiment of $^{177}$Lu Labeled Complex in Normal Mice

The normal mice were randomly divided into experimental group I, experimental group II, control group A and control group B with 3 mice in each group.

$^{177}$Lu complex with purity of greater than 95% was prepared according to the method in Example 31. The complex is obtained by labeling compound 10 in Example 1 with $^{177}$Lu, which was used as medicine B for the experimental group I in the experiment.

With reference to the method in Example 31, $^{177}$Lu labeled compound (II-2) was prepared by substituting compound 10 with the compound (II-2) in Example 2, which was used as medicine D for the experimental group II in the experiment.

$^{177}$Lu-PSMA 617 with purity of greater than 95% was prepared according to a prior method, which was used as medicine A for the control group A in the experiment.

$^{177}$Lu-EB-PSMA 617 with purity of greater than 95% was prepared according to the method in Example 8 in WO2019/165200, which was used as medicine C for the control group B in the experiment.

Figure 2:
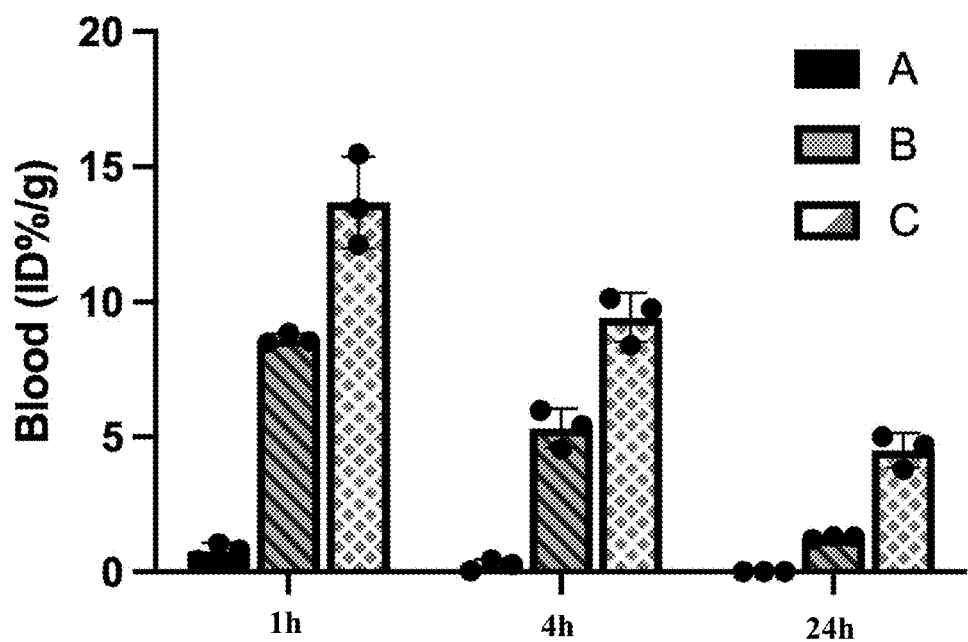
FIG. 2 shows comparison of uptake in the blood of normal mice at different time points after compound in Example 31, $^{177}$Lu-PSMA and $^{177}$Lu-EB-PSMA 617 are injected.

5 MBq of medicine B, medicine D, medicine A and medicine C were intravenously injected into tails of the mice in the first experimental group, the second experimental group, the control group A and the control group B, respectively. The uptake in the blood was measured 1 h, 4 h and 24 h after the injection was completed. Results are shown in FIG. 2 and FIG. 7. SPECT-CT imaging was conducted 1 h, 4 h, 24 h, and 48 h after the injection was completed. Results are shown in FIG. 5 and FIG. 6.

From FIG. 2, the uptake of the $^{177}$Lu complex (B) in Example 31 of the present disclosure in the blood is higher than that in the $^{177}$Lu-PSMA-617 (A) group but much lower than that in the $^{177}$Lu-EB-PSMA-617 (C) group at all tested time points (1 h, 4 h and 24 h). From the comparison of FIG. 7 and FIG. 2, the uptake of the $^{177}$Lu labeled compound (II-2) in the blood is much lower than that in the $^{177}$Lu-EB-PSMA-617 (C) group at all tested time points (1 h, 4 h and 24 h).

FIG. 5 and FIG. 6 are diagrams showing SPECT-CT imaging of normal mice after the $^{177}$Lu complex in Example 31 and the $^{177}$Lu labeled compound (II-2) are injected, respectively.

In summary, compared with existing PSMA-targeting probes, the compound targeting prostate specific membrane antigen provided by the present disclosure has high uptake in tumors, and more importantly has appropriate blood circulation time, so that when the radionuclide labeled compound targeting prostate specific membrane antigen of the present disclosure is used in therapy of prostate cancer, not only can the therapeutic needs of uptake in the blood and uptake in tumors be met, but also hematotoxicity and myelosuppression risks are greatly reduced. The compound has a higher value in clinical application and popularization and is expected to be applied to nuclide therapy and imaging of prostate cancer.

Although the present disclosure has been described in detail by general descriptions, specific embodiments and tests above, it is obvious to persons skilled in the field that some modifications or improvements can be made on the basis of the present disclosure. Therefore, all the modifications or improvements made without departing from the spirit of the present disclosure shall fall within the protection scope of the present disclosure.

The invention claimed is:

1. A compound targeting prostate specific membrane antigen or a pharmaceutically available salt thereof, wherein the molecular structure of the compound targeting prostate specific membrane antigen is shown in Formula (II-1):

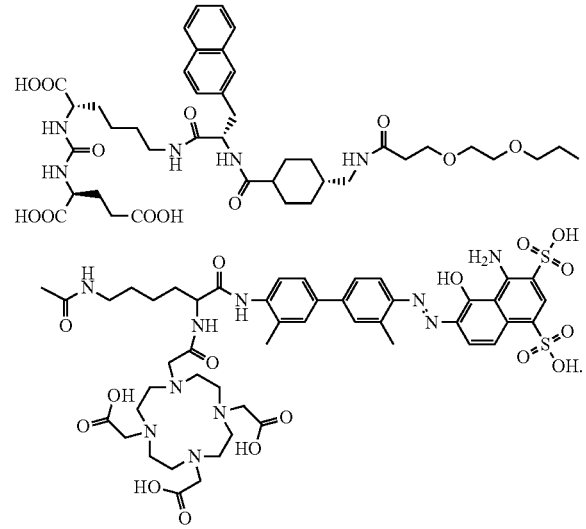

Formula (II-1)

2. A method for preparing a compound targeting prostate specific membrane antigen, comprising the following steps:

introducing a Boc protective group to one end of 4,4'-diamino-3,3'-dimethyl biphenyl, followed by a reaction with 4,6-diamino-5-hydroxy-1,3-naphthalenedisulfonic acid to prepare a truncated Evans Blue derivative; removing the Boc protective group, followed by an amide condensation reaction with Nα-Fmoc-Np-Boc-L-lysine; next, removing the Boc protective group under the action of TFA, followed by an amide condensation reaction with COOH-PEG$_2$-COOH and a reaction with PSMA-617 under the presence of EDC and NHS; then removing an Fmoc protective group using piperazine; and finally, carrying out a reaction with DOTA-NHS to obtain a compound having the following structure shown in Formula (II-1):

Formula (II-1)

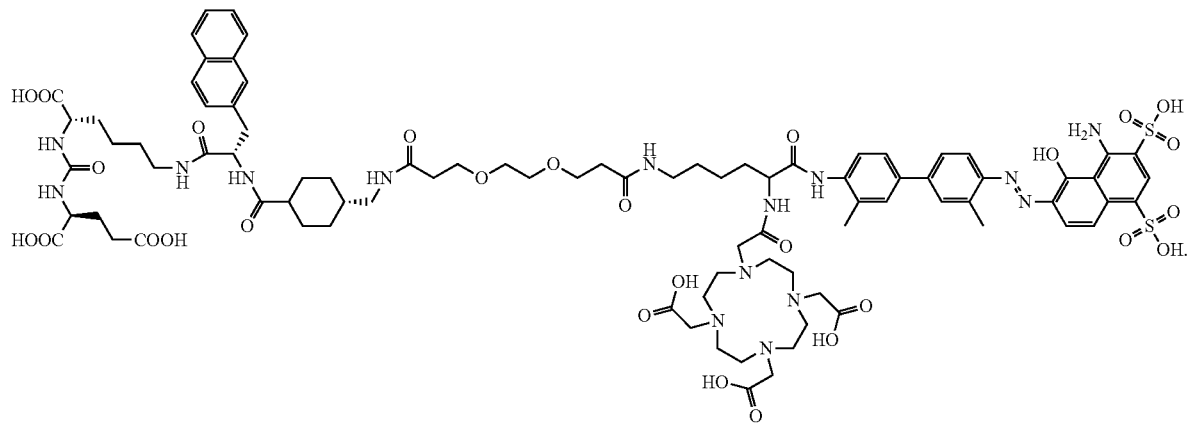

3. A radiolabeled compound targeting prostate specific membrane antigen, wherein the compound is a complex obtained by using the compound shown in Formula (II-1) according to claim 1 as a ligand and labeling the ligand with a radionuclide.

4. The radiolabeled compound according to claim 3, wherein the radionuclide is any one of $^{177}$Lu, $^{90}$Y, $^{18}$F, $^{64}$Cu, $^{68}$Ga $^{62}$Cu, $^{67}$Cu, $^{86}$Y, $^{89}$Zr, $^{99m}$Tc, $^{89}$Sr, $^{153}$Sm, $^{149}$Tb, $^{161}$Tb $^{186}$Re, $^{188}$Re $^{212}$Pb, $^{213}$Bi, $^{223}$Ra, $^{225}$Ac, $^{226}$Th, $^{227}$Th, $^{131}$J, $^{211}$At, or $^{111}$In.

5. The radiolabeled compound according to claim 3, wherein the radionuclide is $^{68}$Ga, $^{177}$Lu, or $^{90}$Y.

6. A method for preparing a radiolabeled compound targeting prostate specific membrane antigen, wherein the method comprises the following steps: dissolving the compound shown in Formula (II-1) according to claim 1 in a buffer solution or deionized water; and adding a radionuclide solution to a resulting solution for a reaction under closed conditions for 5-40 min to produce a radionuclide labeled complex;

or the method comprises the following steps: dissolving an appropriate amount of the compound shown in Formula (II-1) according to claim 1 in a buffer solution or deionized water; treating the obtained solution to aseptic filtration, followed by loading into a container, freeze-drying and sealing with a stopper to obtain a freeze-dried medicine box; and then adding an appropriate amount of an acetic acid solution or a buffer solution to the freeze-dried medicine box for dissolution, and adding a corresponding radionuclide solution for a reaction under closed conditions for 5-40 min to produce a radionuclide labeled complex.

7. A pharmaceutical composition, comprising a compound targeting prostate specific membrane antigen or a pharmaceutically available salt thereof, wherein the molecular structure of the compound targeting prostate specific membrane antigen is shown in Formula (II-1):

Formula (II-1)

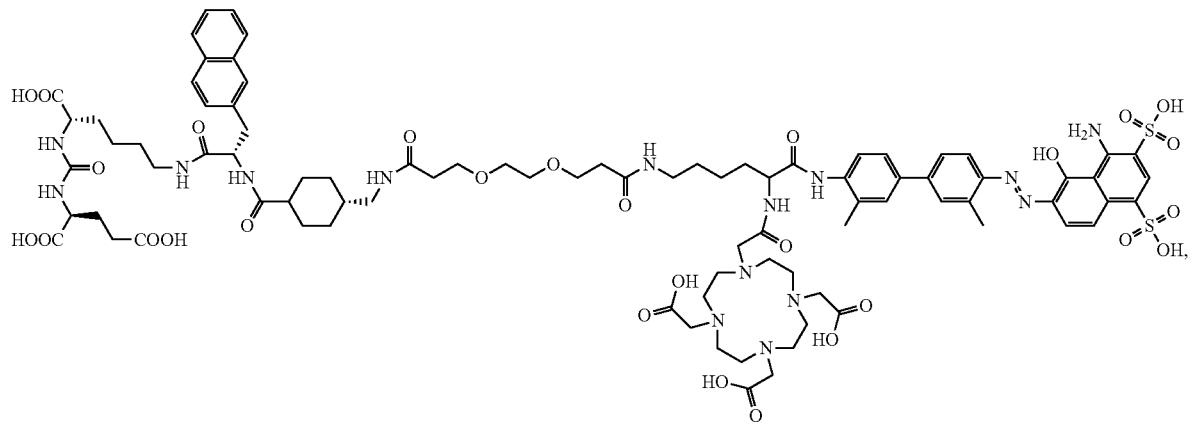

or a radiolabeled compound targeting prostate specific membrane antigen according to claim 6 and a pharmaceutically acceptable carrier.

8. The composition according to claim 7, wherein the pharmaceutically acceptable carrier is selected from an adhesive, a buffer, a colorant, a diluent, a disintegrator, an emulsifier, a flavoring agent, a flow aid, a lubricant, a preservative, a stabilizer, a surfactant, a tabletting agent, a wetting agent, or a combination thereof.

* * * * *